US005514676A

United States Patent [19]
Ulrich et al.

[11] Patent Number: 5,514,676
[45] Date of Patent: May 7, 1996

[54] AMINO-BENZOIC ACIDS AND DERIVATIVES, AND METHODS OF USE

[75] Inventors: Peter C. Ulrich, Old Tappan, N.J.; Anthony Cerami, Shelter Island; Dilip R. Wagle, Valley Cottage, both of N.Y.; Michael E. Lankin, Montclair; David H. Shih, Lawrenceville, both of N.J.; San-Bao Hwang, Sudbury, Mass.

[73] Assignees: The Rockefeller University, New York, N.Y.; Alteon Inc., Ramsey, N.J.

[21] Appl. No.: 383,764

[22] Filed: Feb. 3, 1995

Related U.S. Application Data

[63] Continuation-in-part of Ser. No. 162,538, Dec. 3, 1993, Pat. No. 5,476,849, which is a continuation-in-part of Ser. No. 896,854, Jun. 12, 1992, Pat. No. 5,272,176, which is a division of Ser. No. 561,066, Aug. 1, 1990, Pat. No. 5,137,916, which is a continuation-in-part of Ser. No. 481,869, Feb. 20, 1990, Pat. No. 5,128,360, which is a continuation-in-part of Ser. No. 220,504, Jul. 8, 1988, abandoned, which is a division of Ser. No. 798,032, Nov. 14, 1985, Pat. No. 4,758,583, which is a continuation-in-part of Ser. No. 590,820, Mar. 19, 1984, Pat. No. 4,665,192.

[51] Int. Cl.$^6$ ............... A61K 31/535; A61K 31/495; A61K 31/415; A61K 31/195; A61K 31/165; A61K 31/155

[52] U.S. Cl. ............... 514/231.2; 514/231.5; 514/248; 514/314; 514/399; 514/400; 514/535; 514/561; 514/563; 514/567; 514/617; 514/634; 514/632

[58] Field of Search ............... 514/231.2, 231.5, 514/248, 314, 359, 400, 535, 561, 563, 567, 617, 634, 632

[56] References Cited

U.S. PATENT DOCUMENTS

| 812,554 | 2/1906 | Einhorn et al. | 560/49 |
|---|---|---|---|
| 4,758,583 | 7/1988 | Ceramic et al. | 514/399 |
| 5,137,916 | 8/1992 | Ulrich et al. | 514/535 |

FOREIGN PATENT DOCUMENTS

| 0068407 | 1/1983 | European Pat. Off. |
| 0222313 | 5/1987 | European Pat. Off. |
| 0316852 | 5/1989 | European Pat. Off. |
| 0327919 | 8/1989 | European Pat. Off. |
| 0330263 | 8/1989 | European Pat. Off. |
| 0339496 | 11/1989 | European Pat. Off. |
| 0359112 | 3/1990 | European Pat. Off. |
| 0450598 | 10/1991 | European Pat. Off. |
| 2914935 | 10/1979 | Germany . |
| 3023433 | 1/1981 | Germany . |
| 1197083 | 7/1970 | United Kingdom . |
| 1256235 | 12/1971 | United Kingdom . |
| WO90/06117 | 6/1990 | WIPO . |

OTHER PUBLICATIONS

Baden et al., 1983, "Effect of minoxidil on cultured keratinocytes", J. Invest. Dermatol. 81:558–60.

Brown et al., 1989, Presentation of Abstract for Association for Academic Minority Physicians, Annual Scientific Meeting.

Brownlee et al., 1988, "Advanced Glycosylation Endproducts in Tissue and the Biochemical Baiss of Diabetic Complications", New Eng. J. Med. 318-1315-21.

Brownlee et al., 1986, "Inhibition of Glucose–derived Protein Crosslinking and Prevention of Early Diabetic Changes in Glomerular Basement Memembrane by Aminoguanidine", Diabetes 35 Suppl. 1: 42A.

Brownlee et al., 1983, "Covalent Attachment of Soluble Proteins by Nonenzymatically Glycosylated Collage.", J. Exp. Med. 158:1739–44.

Brownlee et al., 1986, "Aminoguanidine prevents diabetes––induced arterial wall protein cross–linking", Science 232:1629–32.

Bucala et al., 1992, "Advanced Glycosylation: Chemistry, Biology, and Implications for Diabetes and Aging", Advanced in Pharmacology 23:1–34.

Budvari et al., 1989, Merck Index, Eleventh edition, p 69 (434) 72–3 (454), 1230–31 (7763).

Bunn et al., 1975, "Further identification of the nature and linkage of the carbohydrate in hemoglobin $A_{1c}$.", Biochem. Biophys. Res. Comm. 67: 103–9.

Eble et al., 1983, "Nonenzymatic Glucosylation and Glucose–dependent Cross–linking of Protein", J. Biol. Chem. 258: 9406–9412.

Giambione and Brownlee, "aminoguanidien treatment Normalizes Increased Steady–state Levels of Laminin B1 mRNA in Kidneys of Long–term Streptozotocin–diabetic Rats," Diabetes, 38, Supplement 2:83A Forty–ninth Annual Meeting, American Diabetes Association (1989).

Gottschalk, A., In the Glycoproteins (Gottschalk, A., ed) Part A, pp. 141–157, Elsevier Publishing Co., New York (1972).

Hayase et al., 1989, "Aging of Proteins: Immunological Detection of α Glucose–derived Pyrrole Formed during Maillard Reaction in vivo", J. Biol. Chem. 263:3758–64.

Koenig et al., 1977, "Structure of carbohydrate of hemoglobin $A_{1c}$", J. Biol. Chem. 252: 2992–7.

Kohn et al., 1984, "Collagen aging in vitro by nonenzymatic glycosylation and browning", Diabetes 33:57–9.

Kumar et al., 1984, "Syntheses and Anthelmintic Activity of Alkyl 5(6)–(Substituted–carbamoyl)–and 5(6)–(Disubstituted–carbamoyl) benzimidazole–2–carbamates and Related Compounds.", J. Med. Chem. 27:1083–89.

(List continued on next page.)

Primary Examiner—Theodore J. Criares
Attorney, Agent, or Firm—Klauber & Jackson

[57] ABSTRACT

The present invention relates to compounds, compositions and methods for inhibiting nonenzymatic cross-linking (protein aging). Accordingly, a composition is disclosed which comprises an agent capable of inhibiting the formation of advanced glycosylation endproducts of target proteins by reacting with a carbonyl moiety of the early glycosylation product of such target proteins formed by their initial glycosylation. The method comprises contacting the target protein with the composition. Both industrial and therapeutic applications for the invention are envisioned, as food spoilage and animal protein aging can be treated.

60 Claims, No Drawings

OTHER PUBLICATIONS

Madar et al., 1988, "Glucose uptake and conversion into glycogen in isolated diabetic rat aorta under the influence of procaine, Aslavital and Gerovital H3", Chem. Abs. 108:602w.

Maillard, 1912, "Action des acides amines sur le sucres; formation des melanoidines par voie methodique", C.R. Acad. Sci., 154:66–68.

Mihailescu, 1973, "Therapeutical value of glutamic acid and procaine in the evolution of some metabolic changes in alloxan diabetes", Chem. Abs. 79:13515c.

Monnier et al., 1984, "Accelerated Age–related browning of human collagen in diabetes mellitus", Proc. Natl. Acad. Sci. 81:583–7.

Monnier and Cerami, 1983, "Detection of nenzymatic browning products in the human lens", Biochem. Biophys. Acta, 760:97–103.

Monnier and Cerami, 1983, "Nonenzymatic glycosylation and browning of proteins in vivo", in *Maillard Reaction in Food and Nutrition*, Waller, ed. *American Chemical Society* 215:431–49.

Monnier and Ceramic, 1982, "Non–enzymatic glycosylation browning of proteins in diabetes", Clin. Endocrinol. Metab. 11:431–52.

Monnier et al., 1981, "Nonenzymatic Browning in vivo: Possible Process for Aging of Long–Lived Proteins", Science 211:491–93.

Murad et al., 1987, "Suppression of fibroblast proliferation and lysyl hydroylase activity by minoxidil", J. Biol. Chem. 262:11973–78.

Nicholls et al., 1989, "Advanced Glycosylation End–Products in Experimental Murine Diabetic Nephropathy: Effect of Islet Isografting and of Aminoguanidine", Lab. Invest. 60:486.

Nordbo, 1979, "Ability of Chlorhexidine and Benzalkonium Chloride to Catalyze Browning Reactions in vitro" J. Dent. Res. 58:1429.

Gimomi et al., 1989, "Aminoguanidine inhibits 3–deoxyglucosone during the advanced Maillard reaction", Diabetes Res. Clin. Prac. 6:311–13.

Oimomi et al., 1989, "The Effects of Aminoguandine on 3–Deoxyglucosone in the Maillar Reaction", Argric. Biol. Chem., 53:1727–28.

Oxlund and Andressen, 1989, "The increase in biochemical and biomechanical stability of collagen in diabetic rats is prevented by aminoguanidine treatment", European Association for the study of Diabetes, Twenty–fifth Annual Meeting, p. 525A, Abstract No. 371.

Pongor et al., 1984, "Aging of Proteins: Isolation and Identification of a Fluorescent Chromophore from the Reaction of Polypeptides with Glucose", Proc. Natl. Acad. Sci. USA 81:2684–88.

Reynolds, 1965, Adv. Food Res., 14, pp. 167–283.

Sell and Monnier, 1989, "Structure Elucidation of a Senescence Cross–link from Human Extracellular Matrix", J. Biol. Chem. 264:21597–602.

Soulis et al., 1988, N & H Conference on the Maillard reaction in Aging, Diabetes, and Nutrition, Bethesda, MD, Sep. 22–23, p. 30.

AMINO-BENZOIC ACIDS AND DERIVATIVES, AND METHODS OF USE

The present application is a Continuation-In-Part of application Ser. No. 08/162,538, filed Dec. 3, 1993, now U.S. Pat. No. 5,476,849 which is a Continuation-In-Part of application Ser. No. 07/896,854, filed Jun. 12, 1992, now U.S. Pat. No. 5,272,176; which is a division of U.S. Ser. No. 07/561,066, filed Aug. 1, 1990, now U.S Pat. No. 5,137,916; which is a Continuation-In-Part of Ser. No. 07/481,869, filed Feb. 20, 1990, now U.S. Pat. No. 5,128,360; which is a Continuation-In-Part of U.S. Ser. No. 07/220,504, filed Jul. 18, 1988, now abandoned; which is a Division of U.S. Ser. No. 06/798,032, filed Nov. 14, 1985 and now U.S. Pat. No. 4,758,583; which is a Continuation-In-Part of U.S. Ser. No. 06/590,820, filed Mar. 19, 1984, and now U.S. Pat. No. 4,665,192. Applicants claim the benefits of these Applications under 35 U.S.C. §120.

RELATED PUBLICATIONS

Certain of the Applicants are co-authors of the following articles directed to the subject matter of the present invention: "COVALENT ATTACHMENT OF SOLUBLE PROTEINS BY NONENZYMATICALLY GLYCOSYLATED COLLAGEN: ROLE IN THE IN SITU FORMATION OF IMMUNE COMPLEXES", Brownlee et al., *J. Exp. Med.*, 158, pp. 1730–1744 (1983); and "AGING OF PROTEINS: ISOLATION AND IDENTIFICATION OF FLUORESCENT CHROMOPHORE FROM THE REACTION OF POLYPEPTIDES WITH GLUCOSE" Pongor et al., *Proc. Natl. Acad. Sci. U.S.A.*, 81, pp. 2684–2688, (1984), and "ADVANCED GLYCOSYLATION ENDPRODUCTS IN TISSUE AND THE BIOCHEMICAL BASIS OF DIABETIC COMPLICATIONS", Brownlee et al., *The New Eng. J. of Med.*, 318, pp. 1315–1321 (1988).

BACKGROUND OF THE INVENTION

The present invention relates generally to the aging of proteins resulting from their reaction with glucose and other reducing sugars, and more particularly, to the inhibition of the reaction of nonenzymatically glycosylated proteins and the often resultant formation of advanced glycosylation endproducts and cross-links.

The reaction between glucose and proteins has been known for some time. Its earliest manifestation was in the appearance of brown pigments during the cooking of food, which was identified by Maillard in 1912, who observed that glucose or other reducing sugars react with amino acids to form adducts that undergo a series of dehydrations and rearrangements to form stable brown pigments. Maillard, *C.R. Acad. Sci.*, 154, pp. 66–68, (1912). Further studies have suggested that stored and heat treated foods undergo non-enzymatic browning as a result of the reaction between glucose and the polypeptide chain, and that the proteins are resultingly cross-linked and correspondingly exhibit decreased bioavailability.

This reaction between reducing sugars and food proteins was found to have its parallel in vivo. Thus, the nonenzymatic reaction between glucose and the free amino groups on proteins to form a stable, 1-deoxyketosyl adduct, known as the Amadori product, has been shown to occur with hemoglobin, wherein a rearrangement of the amino terminal of the beta-chain of hemoglobin by reaction with glucose, forms the adduct known as hemoglobin $A_{1c}$. The reaction has also been found to occur with a variety of other body proteins, such as lens crystallins, collagen and nerve proteins. See, Bucala et al., "Advanced Glycosylation: Chemistry, Biology, and Implications for Diabetes and Aging," in *Advances in Pharmacology*, Vol. 23, pp. 1–34, Academic Press (1992).

Moreover, brown pigments with spectral and fluorescent properties similar to those of late-stage Maillard products have also been observed in vivo in association with several long-lived proteins, such as lens proteins and collagen from aged individuals. An age-related linear increase in pigment was observed in human dura collagen between the ages of 20 to 90 years. Interestingly, the aging of collagen can be mimicked in vitro by the cross-linking induced by glucose; and the capture of other proteins and the formation of adducts by collagen, also noted, is theorized to occur by a cross-linking reaction, and is believed to account for the observed accumulation of albumin and antibodies in kidney basement membrane.

In parent application Ser. No. 798,032, now U.S. Pat. No. 4,758,583, a method and associated agents were disclosed that served to inhibit the formation of advanced glycosylation endproducts by reacting with the early glycosylation product that results from the original reaction between the target protein and glucose. Accordingly, inhibition was postulated to take place as the reaction between the inhibitor and an early glycosylation product appeared to interrupt the subsequent reaction of the glycosylated protein with additional protein material to form the cross-linked late stage product. One of the agents identified as an inhibitor was aminoguanidine, and the results of further testing have borne out its efficacy in this regard.

While the success that has been achieved with aminoguanidine and similar compounds is promising, a need continues to exist to identify and develop additional inhibitors that broaden the availability and perhaps the scope of this potential activity and its diagnostic and therapeutic utility.

SUMMARY OF THE INVENTION

In accordance with the present invention, a method and compositions are disclosed for the inhibition of the advanced glycosylation of proteins (protein aging). In particular, the compositions comprise agents for inhibiting nonenzymatic cross-linking (protein aging) due to the formation of advanced glycosylation endproducts. The agents may be selected from those materials capable of reacting with the early glycosylation product from the reaction of glucose with proteins and preventing further reactions. Cross-linking caused by other reactive sugars present in vivo or in foodstuffs, including ribose, galactose and fructose would also be prevented by the methods and compositions of the present invention.

The agents comprise compounds having the following structural formula:

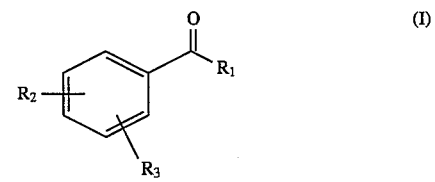

(I)

wherein $R_1$ is a hydroxy, lower alkoxy, amino or hydrazino group, or a group of the formula

—NR₄R₅, wherein R₄ is hydrogen or lower alkyl, and R₅ is an alkyl group of 1–20 carbon atoms, an aryl group, a hydroxy lower alkyl group, a cycloloweralkyl group or a heterocyclic group containing 4–7 ring members and 1–3 heteroatoms; or R₄ and R₅ together with the nitrogen form a morpholino, piperidinyl, or piperazinyl group; or when R₄ is hydrogen, then R₅ can also be a hydroxy group;

> R₂ is 0–3 amino or nitro groups, and/or a hydrazino group, a hydrazinosulfonyl group, a hydroxyethylamino or an amidino group;
>
> R₃ is hydrogen or one or two fluoro, hydroxy, lower alkoxy, carboxy, loweralkylamino, dilower alkylamino or hydroxy loweralkylamino groups;
>
> with the proviso that when R₁ is hydroxy or lower alkoxy, then R₃ is a non-hydrogen substituent;
>
> with the further proviso that when R₁ is hydrazino, then there must be at least two non-hydrogen substituents on the phenyl ring;
>
> and with the further proviso that when R₃ is hydrogen, then R₅ can also be an aminoimino, guanidyl, aminoguanidinyl or diaminoguanidyl group;
>
> their pharmaceutically acceptable acid addition salts and hydrates; and mixtures thereof, and
>
> a carrier therefor.

The compounds utilized in the compositions of this invention appear to react with an early glycosylation product thereby preventing the same from later forming the advanced glycosylation end products which lead to protein cross-links, and thereby, to protein aging.

The present invention also relates to a method for inhibiting protein aging by contacting the initially glycosylated protein at the stage of the early glycosylation product with a quantity of one or more of the agents of the present invention, or a composition containing the same. In the instance where the present method has industrial application, one or more of the agents may be applied to the proteins in question, either by introduction into a mixture of the same in the instance of a protein extract, or by application or introduction into foodstuffs containing the protein or proteins, all to prevent premature aging and spoilage of the particular foodstuffs.

The ability to inhibit the formation of advanced glycosylation endproducts carries with it significant implications in all applications where protein aging is a serious detriment. Thus, in the area of food technology, the retardation of food spoilage would confer an obvious economic and social benefit by making certain foods of marginal stability less perishable and therefore more available for consumers. Spoilage would be reduced as would the expense of inspection, removal, and replacement, and the extended availability of the foods could aid in stabilizing their price in the marketplace. Similarly, in other industrial applications where the perishability of proteins is a problem, the admixture of the agents of the present invention in compositions containing such proteins would facilitate the extended useful life of the same. Presently used food preservatives and discoloration preventatives such as sulfur dioxide, known to cause toxicity including allergy and asthma in animals, can be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as a consequence of diabetes. Accordingly, the ability to either retard or substantially inhibit the formation of advanced glycosylation endproducts carries the promise of treatment for diabetes and, of course, improving the quality and, perhaps, duration of animal life.

The present agents are also useful in the area of personal appearance and hygiene, as they prevent the staining of teeth by cationic anti-microbial agents with anti-plaque properties, such as chlorhexidine.

Accordingly, it is a principal object of the present invention to provide a method for inhibiting the extensive cross-linking of proteins that occurs as an ultimate consequence of the reaction of the proteins with glucose and other reactive sugars, by correspondingly inhibiting the formation of advanced glycosylation endproducts.

It is a further object of the present invention to provide a method as aforesaid which is characterized by a reaction with an initially glycosylated protein identified as an early glycosylation product.

It is a further object of the present invention to provide a method as aforesaid which prevents the rearrangement and cross-linking of the said early glycosylation products to form the said advanced glycosylation endproducts.

It is a yet further object of the present invention to provide agents capable of participating in the reaction with the said early glycosylation products in the method as aforesaid.

It is a still further object of the present invention to provide therapeutic methods of treating the adverse consequences of protein aging by resort to the aforesaid method and agents.

It is a still further object of the present invention to provide a method of inhibiting the discoloration of teeth by resort to the aforesaid method and agents.

It is a still further object of the present invention to provide compositions including pharmaceutical compositions, all incorporating the agents of the present invention.

It is a still further object of the present invention to provide novel compounds useful in the methods of this invention, as well as processes for their preparation.

Other objects and advantages will become apparent to those skilled in the art from a consideration of the ensuing description.

DETAILED DESCRIPTION OF THE PREFERRED EMBODIMENT

In accordance with the present invention, agents, compositions, including pharmaceutical compositions containing said agents, and associated methods, have been developed which are believed to inhibit the formation of advanced glycosylation endproducts in a number of target proteins existing in both animals and plant material. In particular, the invention relates to a composition which may contain one or more agents comprising compounds having the structural formula

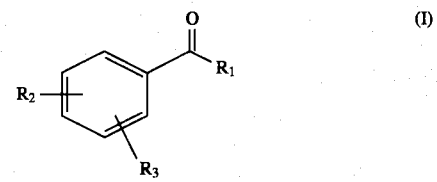

(I)

wherein

R₁ is a hydroxy, lower alkoxy, amino or hydrazino group, or a group of the formula

—NR$_4$R$_5$, wherein R$_4$ is hydrogen or lower alkyl, and R$_5$ is an alkyl group of 1–20 carbon atoms, an aryl group, a hydroxy lower alkyl group, a cycloloweralkyl group or a heterocyclic group containing 4–7 ring members and 1–3 heteroatoms; or R$_4$ and R$_5$ together with the nitrogen form a morpholino, piperidinyl, or piperazinyl group; or when R$_4$ is hydrogen, then R$_5$ can also be a hydroxy group;

R$_2$ is 0–3 amino or nitro groups, and/or a hydrazino group, a hydrazinosulfonyl group, a hydroxyethylamino or an amidino group;

R$_3$ is hydrogen or one or two fluoro, hydroxy, lower alkoxy, carboxy, loweralkylamino, dilower alkylamino or a hydroxyloweralkylamino groups;

with the proviso that when R, is hydroxy or lower alkoxy, then R$_3$ is a non-hydrogen substituent;

with the further proviso that when R$_1$ is hydrazino, then there must be at least two non-hydrogen substituents on the phenyl ring;

and with the further proviso that when R$_3$ is hydrogen, then R$_5$ can also be an aminoimino, guanidyl, aminoguanidinyl or diaminoguanidyl group;

their pharmaceutically acceptable salts and hydrates; and mixtures thereof, and a carrier therefor.

The lower alkyl groups referred to herein contain 1–6 carbon atoms and include methyl, ethyl, propyl, butyl, pentyl, hexyl, and the corresponding branched-chain isomers thereof. The cycloalkyl groups contain 4–7 carbon atoms and are exemplified by groups such as cyclobutyl, cyclopentyl, cyclohexyl, 4-methylcyclohexyl and cycloheptyl groups.

The heterocyclic groups referred to herein include 4–7 membered rings having at least one and up to 3 heteroatoms, e.g., oxygen, nitrogen, or sulfur, therein, and including various degrees of unsaturation. Representatives of such heterocyclic groups are those such as morpholino, piperidino, homopiperidino, piperazino, methylpiperazino, hexamethylenimino, pyridyl, methylpyridyl, imidazolyl, pyrrolidinyl, 2,6-dimethylmorpholino, furfural, 1,2,4-triazolyl, thiazolyl, thiazolinyl, methylthiazolyl, and the like.

Equivalent to the compounds of Formula I for the purposes of this invention are the biocompatible and pharmaceutically acceptable salts and hydrates thereof. Such salts can be derived from a variety of organic and inorganic acids, including, but not limited to, methanesulfonic, hydrochloric, hydrobromic, hydroiodic, toluenesulfonic, sulfuric, maleic, acetic and phosphoric acids.

When the compounds of Formula I contain one or more asymmetric carbon atoms, mixtures of enantiomers, as well as the pure (R) or (S) enantiomeric form can be utilized in the practice of this invention.

Of the compounds encompassed by Formula I, certain combinations of substituents are preferred. For instance, compounds having a 3,4-diamino-, 3-hydroxy-4-amino-, 3-amino-4-hydroxy-, 3,5-diamino-4-hydroxy-, 3,5-diamino-4-alkoxy- or 2,3-diamino-5-fluoro substituent pattern on the phenyl ring are highly preferred.

Representative compounds of the present invention are:
4-(cyclohexylamino-carbonyl)-o-phenylene diamine hydrochloride;
4-aminobenzhydrazide;
3,4-diaminobenzhydrazide;
4-(n-butylamino-carbonyl)-o-phenylene-diamine dihydrochloride;
4-(ethylamino-carbonyl)-o-phenylene-diamine dihydrochloride;
4-carbamoyl-o-phenylene diamine hydrochloride;
4-hydroxybenzhydrazide;
3-amino-4-hydroxybenzoic acid;
4-amino-3-hydroxybenzoic acid;
3-amino-4-hydroxybenzhydrazide;
3-amino-4-hydroxybenzhydrazide dihydrochloride;
4-amidinobenzamide hydrochloride;
4-(morpholino-carbonyl)-o-phenylene-diamine hydrochloride;
4-[(4-morpholino)hydrazino-carbonyl]-o-phenylenediamine;
4-(1-piperidinylamino-carbonyl)-o-phenylenediamine dihydrochloride;
2,4-diamino-3-hydroxybenzoic acid;
3,5-diamino-4-hydroxybenzoic acid;
4-amino-3-hydroxybenzoic acid;
4-amino-3-hydroxybenzamide;
4,5-diamino-2-hydroxybenzoic acid;
3,4-diaminobenzamide;
3,4-diaminobenzhydrazide;
3,4-diamino-N,N-bis(1-methylethyl)benzamide;
3,4-diamino-N,N-diethylbenzamide;
3,4-diamino-N,N-dipropylbenzamide;
3,4-diamino-N-(2-furanylmethyl)benzamide
3,4-diamino-N-(2-methylpropyl)benzamide;
3,4-diamino-N-(4,5-dihydro-2-thiazolyl)benzamide;
3,4-diamino-N-(5-methyl-2-thiazolyl)benzamide;
3,4-diamino-N-(6-methoxy-2-benzothiazolyl)benzamide;
3,4-diamino-N-(6-methoxy-8-quinolinyl)benzamide;
3,4-diamino-N-(6-methyl-2-pyridinyl)benzamide;
3,4-diamino-N-(1H-benzimidazol-2-yl)benzamide;
3,4-diamino-N-(2-pyridinyl)benzamide;
3,4-diamino-N-(2-thiazolyl)benzamide;
3,4-diamino-N-(4-pyridinyl)benzamide;
3,4-diamino-N-[9H-pyrido(3,4-b)indol-6-yl] benzamide
3,4-diamino-N-butylbenzamide;
3,4-diamino-N-cyclohexylbenzamide;
3,4-diamino-N-cyclopentylbenzamide;
3,4-diamino-N-decylbenzamide;
3,4-diamino-N-dodecylbenzamide;
3,4-diamino-N-methylbenzamide;
3,4-diamino-N-octylbenzamide;
3,4-diamino-N-pentylbenzamide;
3,4-diamino-N-phenylbenzamide;
3-amino-4-hydroxybenzamide;
3-amino-4-hydroxy-N-octylbenzamide;
4-(diethylamino-carbonyl)-o-phenylene diamine;
4-(tert-butylamino-carbonyl)-o-phenylene diamine;
4-isobutylamino-carbonyl)-o-phenylene diamine;
4-(neopentylamino-carbonyl)-o-phenylene diamine;
4-(dipropylamino-carbonyl)-o-phenylene diamine;
4-(n-hexylamino-carbonyl)-o-phenylene diamine;
4-(n-decylamino-carbonyl)-o-phenylene diamine;
4-(n-dodecylamino-carbonyl)-o-phenylene diamine;
4-(1-hexadecylamino-carbonyl)-o-phenylene diamine;
4-(octadecylamino-carbonyl)-o-phenylene diamine;
4-(hydroxylamino-carbonyl)-o-phenylene diamine;
4-(2-hydroxyethylamino-carbonyl)-o-phenylene diamine;
4-[(2-hydroxyethylamino)ethylamino-carbonyl]o-phenylene diamine;
4-[(2-hydroxyethyloxy)ethylamino-carbonyl]-o-phenylene diamine;
4-(6-hydroxyhexylamino-carbonyl)-o-phenylene diamine;
4-(3-ethoxypropylamino-carbonyl)-o-phenylene diamine;
4-(3-isopropoxypropylamino-carbonyl)-o-phenylene diamine;

4-(3-dimethylaminopropylamino-carbonyl)-o-phenylene diamine;
4-(N,N,2,2-tetramethyl-1,3-propanoamino-carbonyl)-o-phenylene diamine;
4-[4-(2-aminoethyl)morpholino-carbonyl]-o-phenylene diamine;
4-[4-(3-aminopropyl)morpholino-carbonyl]-o-phenylene diamine;
4-[N-(3-aminopropyl)pyrrolidino-carbonyl]-o-phenylene diamine;
4-[3-(N-piperidino)propylamino-carbonyl]-o-phenylene diamine;
4-[3-(4-methylpiperazinyl)propylamino-carbonyl]-o-phenylene diamine;
4-(3-imidazoylpropylamino-carbonyl)-o-phenylene diamine;
4-(3-phenylpropylamino-carbonyl)-o-phenylene diamine;
4-[2-(N,N-diethylamino)ethylamino-carbonyl]-o-phenylene diamine;
4-(imidazolylamino-carbonyl)-o-phenylene diamine;
4-(pyrrolidinyl-carbonyl)-o-phenylene diamine;
4-(piperidino-carbonyl)-o-phenylene diamine;
4-(1-methylpiperazinyl-carbonyl)-o-phenylene diamine;
4-(2,6-dimethylmorpholino-carbonyl)-o-phenylene diamine;
4-(pyrrolidin-1-ylamino-carbonyl)-o-phenylene diamine;
4-(homopiperidin-1-ylamino-carbonyl)-o-phenylene diamine;
4-(4-methylpiperazine-1-ylamino-carbonyl)-o-phenylene diamine;
4-(1,2,4-triazol-1-ylamino-carbonyl)-o-phenylene diamine;
4-(guanidinyl-carbonyl)-o-phenylene diamine;
4-(guanidinylamino-carbonyl)-o-phenylene diamine;
4-(aminoguanidinylamino-carbonyl)-o-phenylene diamine;
4-(diaminoguanidinylamino-carbonyl)-o-phenylene diamine;
2-hydroxy-4-(diethylamino-carbonyl)aniline;
2-hydroxy-4-(tertbutylamino-carbonyl)aniline;
2-hydroxy-4-(isobutylamino-carbonyl)aniline;
2-hydroxy-4-(neopentylamino-carbonyl)aniline;
2-hydroxy-4-(dipropylamino-carbonyl)aniline;
2-hydroxy-4-(n-hexylamino-carbonyl)aniline;
2-hydroxy-4-(n-decylamino-carbonyl)aniline;
2-hydroxy-4-(n-dodecylamino-carbonyl)aniline;
2-hydroxy-4-(1-hexadecylamino-carbonyl)aniline;
2-hydroxy-4-(octadecylamino-carbonyl)aniline;
2-hydroxy-4-(hydroxylamino-carbonyl)aniline;
2-hydroxy-4-(2-hydroxyethylamino-carbonyl)aniline;
2-hydroxy-4-((2-hydroxyethylamino)ethylamino-carbonyl) aniline;
2-hydroxy-4-((2-hydroxyethyloxy)ethylamino-carbonyl)aniline;
2-hydroxy-4-(6-hydroxyhexylamino-carbonyl)aniline;
2-hydroxy-4-(3-ethoxypropylamino-carbonyl)aniline;
2-hydroxy-4-(3-isopropoxypropylamino-carbonyl)aniline;
2-hydroxy-4-(3-dimethylaminopropyl amino-carbonyl)aniline;
2-hydroxy-4-(N,N,2,2-tetramethyl-1,3-propanoamino-carbonyl)aniline;
2-hydroxy-4-(4-(2-aminoethyl)morpholino-carbonyl)aniline;
2-hydroxy-4-[4-(3-aminopropyl)morpholino-carbonyl] aniline;
2-hydroxy-4-[N-(3-aminopropyl)pyrrolidino-carbonyl] aniline;
2-hydroxy-4-[3-(N-piperidino)propylamino-carbonyl] aniline propane;
2-hydroxy-4-[3-(4-methylpiperazinyl)propylamino-carbonyl] aniline;
2-hydroxy-4-(3-imidazoylpropylamino-carbonyl)aniline;
2-hydroxy-4-(3-phenylpropylamino-carbonyl)aniline;
2-hydroxy-4-[2-(N,N-diethylamino)ethylamino-carbonyl] aniline;
2-hydroxy-4-(imidazolylamino-carbonyl)aniline;
2-hydroxy-4-(pyrrolidinyl-carbonyl)aniline;
2-hydroxy-4-(piperidino-carbonyl)aniline;
2-hydroxy-4-(1-methylpiperazinyl-carbonyl)aniline;
2-hydroxy-4-(2,6-dimethylmorpholino-carbonyl)aniline;
2-hydroxy-4-(pyrrolidin-1-ylamino-carbonyl)aniline;
2-hydroxy-4-(homopiperidin-1-ylamino-carbonyl)aniline;
2-hydroxy-4-(4-methylpiperazine-1-ylamino-carbonyl)aniline;
2-hydroxy-4-(1,2,4-triazol-1-ylamino-carbonyl)aniline;
2-hydroxy-4-(guanidinyl-carbonyl)aniline;
2-hydroxy-4-(guanidinylamino-carbonyl)aniline;
2-hydroxy-4-(aminoguanidinylamino-carbonyl)aniline;
2-hydroxy-4-(diaminoguanidinylamino-carbonyl)aniline;
3,5-diamino-4-hydroxybenzoic acid;
3,4,5-triaminobenzamide;
3,5-diaminosalicylic acid;
3,5-diamino-2-methylbenzoic acid;
5-aminoisophthalic acid;
3-aminophthalic acid;
3-hydroxyanthranilic acid;
3,5-diamino-4-methyl benzoic acid;
3,4-aminosalicylic acid;
4-aminosalicylic acid;
5-aminosalicylic acid;
4-guanidinobenzoic acid;
4,5-difluoroanthranilic acid;
4-fluoro-3-nitrobenzoic acid;
3-amino-2,5,6-trifluorobenzoic acid;
2-fluoro-5-nitrobenzoic acid;
methyl 3,5-diamino-4-hydroxy benzoate;
3-amino-5-nitrosalicylic acid;
2,4-dihydroxy-3,5-dinitrobenzoic acid;
3,5-dinitro-4-hydroxybenzoic acid;
methyl 3,5-dinitro-4-hydroxybenzoate;
ethyl 3,5-dinitro-4-hydroxybenzoate;
3,5-dinitro-p-toluic acid;
3,5-dinitrosalicylic acid;
methyl 3-amino-5-nitrosalicylate;
2-amino-3-methylbenzoic acid;
4-amino-3-methoxybenzoic acid;
2-amino-4,5-dimethoxybenzoic acid;
3,5-diaminobenzoic acid;
2-aminoterephthalic acid;
methyl 3,5-diamino-2,4-dihydroxybenzoate;
3-amino-4-fluorobenzoic acid;
isopropyl-3,5-dinitro-4-hydroxybenzoate;
methyl 4-aminosalicylate;
4-aminosalicylhydrazide;
4-(3,5-diamino-4-hydroxybenzoyl)-morpholine;
3,5-diamino-4-fluorobenzoic acid;
ethyl 3,5-diamino-4-hydroxybenzoate;
isopropyl 3,5-diamino-2,4-dihydroxybenzoate;
5-amino-2-fluorobenzoic acid;
3,5-diamino-4-hydroxybenzanilide;
isopropyl 3,5-diamino-4-methylbenzoate;
ethyl 3,5-diamino-4-ethoxybenzoate;
isopropyl 3,5-diamino-4-isopropyloxybenzoate;
3,5-diamino-4-methoxybenzoic acid;
3,5-diamino-4-methylbenzhydrazide;
3,5-diamino-4-methoxybenzhydrazide;

isopropyl 3,4-diaminobenzoate;
methyl 3-amino-4-hydrazinobenzoate
5-aminosalicylic acid;
methyl 3,5-diamino-4-methoxybenzoate;
3,4-diaminobenzohydroxamic acid;
3,5-diamino-4-methylaminobenzoic acid;
3,5-diamino-4-isopropylaminobenzoic acid;
3,5-diamino-4-dimethylaminobenzoic acid;
methyl 3-amino-4-fluorobenzoate;
3,5-diamino-4-isopropyloxybenzhydrazide;
isopropyl 3-amino-4-hydrazinobenzoate;
3-amino-4-fluorobenzhydrazide;
3,5-diamino-4-isopropyloxybenzoic acid;
3,5-diamino-4-hydroxyethylaminobenzoic acid;
3,4,5-triaminobenzoic acid;
2,3-diamino-5-fluoro-benzoic acid; and their pharmaceutically acceptable salts and hydrates.

The above compounds are capable of inhibiting the formation of advanced glycosylation endproducts on target proteins. The cross-linking of the protein to form the advanced glycosylation endproduct contributes to the entrapment of other proteins and results in the development in vivo of conditions such as reduced elasticity and wrinkling of the skin, certain kidney diseases, atherosclerosis, osteoarthritis and the like.

Similarly, plant material that undergoes nonenzymatic browning deteriorates and, in the case of foodstuffs, become spoiled or toughened and, consequently, inedible. Thus, the compounds employed in accordance with this invention inhibit this late stage Maillard effect and intervene in the deleterious changes described above.

The rationale of the present invention is to use agents which block the post-glycosylation step, i.e., the formation of fluorescent chromophores, the presence of which chromophores is associated with, and leads to adverse sequelae of diabetes and aging. An ideal agent would prevent the formation of the chromophore and its associate cross-links of proteins to proteins and trapping of proteins on the other proteins, such as occurs in arteries and in the kidney.

The chemical nature of the early glycosylation products with which the compounds of the present invention are believed to react, may vary, and accordingly, the term "early glycosylation product(s)" as used herein is intended to include any and all such variations within its scope. For example, early glycosylation products with carbonyl moieties that are involved in the formation of advanced glycosylation endproducts, and that may be blocked by reaction with the compounds of the present invention, have been postulated. In one embodiment, it is envisioned that the early glycosylation product may comprise the reactive carbonyl moieties of Amadori products or their further condensation, dehydration and/or rearrangement products, which may condense to form advanced glycosylation endproducts. In another scenario, reactive carbonyl compounds, containing one or more carbonyl moieties (such as glycolaldehyde, glyceraldehyde or 3-deoxyglucosone) may form from the cleavage of Amadori or other early glycosylation endproducts, and by subsequent reactions with an amine or Amadori product, may form carbonyl containing advanced glycosylation products such as alkylformyl-glycosylpyrroles.

Several investigators have studied the mechanism of advanced glycosylation product formation. In vitro studies by Eble et al., (1983), "Nonenzymatic Glucosylation and Glucose-dependent Cross-linking of Protein", *J. Biol. Chem.*, 258:9406–9412, concerned the cross-linking of glycosylated protein with nonglycosylated protein in the absence of glucose. Eble et al. sought to elucidate the mechanism of the Maillard reaction and accordingly conducted controlled initial glycosylation of RNAase as a model system, which was then examined under varying conditions. In one aspect, the glycosylated protein material was isolated and placed in a glucose-free environment and thereby observed to determine the extent of cross-linking.

Eble et al. thereby observed that cross-linking continued to occur not only with the glycosylated protein but with non-glycosylated proteins as well. One of the observations noted by Eble et al. was that the reaction between glycosylated protein and the protein material appeared to occur at the location on the protein chain of the amino acid lysine. Confirmatory experimentation conducted by Eble et al. in this connection demonstrated that free lysine would compete with the lysine on RNAase for the binding of glycosylated protein. Thus, it might be inferred from these data that lysine may serve as an inhibitor of advanced glycosylation; however, this conclusion and the underlying observations leading to it should be taken in the relatively limited context of the model system prepared and examined by Eble et al. Clearly, Eble et al. does not appreciate, nor is there a suggestion therein, of the discoveries that underlie the present invention, with respect to the inhibition of advanced glycosylation of proteins both in vitro and in vivo.

The experiments of Eble et al. do not suggest the reactive cleavage product mechanism or any other mechanism in the in vivo formation of advanced glycosylation endproducts in which glucose is always present. In fact, other investigators support this mechanism to explain the formation of advanced glycosylated endproducts in vivo (see, for example, Hayase et al., *J. Biol. Chem.*, 263, pp. 3758–3764 (1989); Sell and Monnier, *J. Biol. Chem.*, 264, pp. 21597–21602 (1989); Oimomi et al., *Agric. Biol. Chem.*, 53(6):1727–1728 (1989); and *Diabetes Research and Clinical Practice*, 6:311–313 (1989). Accordingly, the use of lysine as an inhibitor in the Eble et al. model system has no bearing upon the utility of the compounds of the present invention in the inhibition of advanced glycosylated endproducts formation in the presence of glucose in vivo, and the amelioration of complications of diabetes and aging.

The compositions useful in the present invention comprise or contain agents capable of reacting with the active carbonyl intermediate of an early glycosylation product. Suitable agents are the compounds of Formula I of the present invention.

The present invention likewise relates to methods for inhibiting the formation of advanced glycosylation endproducts, which comprise contacting the target proteins with a composition of the present invention. In the instance where the target proteins are contained in foodstuffs, whether of plant or animal origin, these foodstuffs could have applied to them by various conventional means a composition containing the present agents.

In the food industry, sulfites were found years ago to inhibit the Maillard reaction and are commonly used in processed and stored foods. Recently, however, sulfites in food have been implicated in severe and even fatal reactions in asthmatics. As a consequence, the sulfite treatment of fresh fruits and vegetables has been banned. The mechanism for the allergic reaction is not known. Accordingly, the present compositions and agents offer a nontoxic alternative to sulfites in the treatment of foods in this manner.

As is apparent from a discussion of the environment of the present invention, the present methods and compositions hold the promise for arresting the aging of key proteins both in animals and plants, and concomitantly, conferring both economic and medical benefits as a result thereof. In the instance of foodstuffs, the administration of the present composition holds the promise for retarding food spoilage thereby making foodstuffs of increased shelf life and greater availability to consumers. Replacement of currently-used preservatives, such as sulfur dioxide known to cause allergies and asthma in humans, with non-toxic, biocompatible compounds is a further advantage of the present invention.

The therapeutic implications of the present invention relate to the arrest of the aging process which has, as indicated earlier, been identified in the aging of key proteins by advanced glycosylation and cross-linking. Thus, body proteins, and particularly structural body proteins, such as collagen, elastin, lens proteins, nerve proteins, kidney glomerular basement membranes and other extravascular matrix components would all benefit in their longevity and operation from the practice of the present invention. The present invention thus reduces the incidence of pathologies involving the entrapment of proteins by cross-linked target proteins, such as retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies.

Protein cross-linking through advanced glycosylation product formation can decrease solubility of structural proteins such as collagen in vessel walls (see Brownlee et al., Science, 232, pp. 1629–1632, (1986)), and can also trap serum proteins, such as lipoproteins to the collagen. Also, this may result in increased permeability of the endothelium and consequently covalent trapping of extravasated plasma proteins in subendothelial matrix, and reduction in susceptibility of both plasma and matrix proteins to physiologic degradation by enzymes. (See Brownlee et al., Diabetes, 35, Suppl. 1, p. 42A (1986)). For these reasons, the progressive occlusion of diabetic vessels induced by chronic hyperglycemia has been hypothesized to result from excessive formation of glucose-derived cross-links. Such diabetic microvascular changes and microvascular occlusion can be effectively prevented by chemical inhibition of advanced glycosylation product formation utilizing a composition and the methods of the present invention.

Studies indicate that the development of chronic diabetic damage in target organs is primarily linked to hyperglycemia so that tight metabolic control would delay or even prevent end-organ damage. See Nicholls et al., Lab. Invest., 60, No. 4, p. 486 (1989), which discusses the effects of islet isografting and aminoguanidine in murine diabetic nephropathy. These studies further evidence that aminoguanidine diminishes aortic wall protein cross-linking in diabetic rats and confirm earlier studies by Brownlee et al., Science, 232, pp. 1629–1632 (1986) to this additional target organ of complication of diabetes. Also, an additional study showed the reduction of immunoglobulin trapping in the kidney by aminoguanidine (Brownlee et al., Diabetes, 35, Suppl. 1, p. 42A (1986)).

Further evidence in the streptozotocin-diabetic rat model that aminoguanidine administration intervenes in the development of diabetic nephropathy was presented by Brownlee et al., 1988, supra, with regard to morphologic changes in the kidney which are hallmarks of diabetic renal disease. These investigators reported that the increased glomerular basement membrane thickness, a major structural abnormality characteristic of diabetic renal disease, was prevented with aminoguanidine.

Taken together, these data strongly suggest that inhibition of the formation of advanced glycosylation endproducts (AGEs), by the teaching of the present invention, may prevent late, as well as early, structural lesions due to diabetes, as well as changes during aging caused by the formation of AGE's.

Diabetes-induced changes in the deformability of red blood cells, leading to more rigid cell membranes, is another manifestation of cross-linking and aminoguanidine has been shown to prevent it in vivo. In such studies, New Zealand White rabbits, with induced, long-term diabetes are used to study the effects of a test compound on red blood cell (RBC) deformability (df). The test compound is administered at a rate of 100 mg/kg by oral gavage to diabetic rabbits (Brown et al., Presentation of Abstract for Association for Academic Minority Physicians, Annual Scientific Meeting (1989)).

Increased cross-linking of collagen in diabetic rats has shown to be prevented by aminoguanidine. Oxlund and Andreassen, "The increase in biochemical and biomechanical stability of collagen in diabetic rats is prevented by aminoguanidine treatment", European Association for the Study of Diabetes, Twenty-fifth Annual Meeting, p. 525A, Abstract No. 371, 1989 showed the effect when thermal stability of tendon fibers was assessed by breaking time in a urea bath, as well as mechanical strength. Soulis et al., "Aminoguanidine reduces tissue fluorescence but not albuminuria in diabetic rats". NIH Conference on the Maillard Reaction in Aging, Diabetes, and Nutrition, Bethesda, Md., Sep. 22–23, 1988, page 30) showed the same effect on collagen in the aorta, measured by fluorescence and solubility.

Giambione and Brownlee, "Aminoguanidine Treatment Normalizes Increased Steady-state Levels of Laminin B1 mRNA in Kidneys of Long-term Streptozotocin-diabetic Rats" Diabetes, 38, Supplement 2:83A Forty-ninth Annual Meeting, American Diabetes Association (1989) showed that aminoguanidine treatment to diabetic rats prevents the diabetes-induced increase in laminin $B_1$ mRNA in the kidney. This indicates that aminoguanidine may prevent overproduction of matrix, which leads to basement membrane thickening and morphologic and functional deterioration of vasculature in kidneys and other organs.

A further consequence of diabetes is the hyperglycemia-induced matrix bone differentiation resulting in decreased bone formation usually associated with chronic diabetes. In animal models, diabetes reduces matrix-induced bone differentiation by 70% (Am. J. Phys., 238 (1980)).

In the instance where the compositions of the present invention are utilized for in vivo or therapeutic purposes, it may be noted that the compounds or agents used therein are biocompatible. Pharmaceutical compositions may be prepared with a therapeutically effective quantity of the agents or compounds of the present invention and may include a pharmaceutically acceptable carrier, selected from known materials utilized for this purpose. Such compositions may be prepared in a variety of forms, depending on the method of administration. Also, various pharmaceutically acceptable addition salts of the compounds of Formula I may be utilized.

A liquid form would be utilized in the instance where administration is by intravenous, intramuscular or intraperitoneal injection. When appropriate, solid dosage forms such as tablets, capsules, or liquid dosage formulations such as solutions and suspensions, etc., may be prepared for oral administration. For topical or dermal application to the skin or eye, a solution, a lotion or ointment may be formulated with the agent in a suitable vehicle such as water, ethanol, propylene glycol, perhaps including a carrier to aid in penetration into the skin or eye. For example, a topical preparation could include up to about 10% of the compound of Formula I. Other suitable forms for administration to other body tissues are also contemplated.

In the instance where the present method has therapeutic application, the animal host intended for treatment may have administered to it a quantity of one or more of the agents, in a suitable pharmaceutical form.

Administration may be accomplished by known techniques, such as oral, topical and parenteral techniques such as intradermal, subcutaneous, intravenous or intraperitoneal injection, as well as by other conventional means. Administration of the agents may take place over an extended period of time at a dosage level of, for example, up to about 25 mg/kg.

As noted earlier, the invention also extends to a method of inhibiting the discoloration of teeth resulting from nonenzymatic browning in the oral cavity which comprises administration to a subject in need of such therapy an amount effective to inhibit the formation of advanced glycosylation endproducts of a composition comprising an agent of structural Formula I.

The nonenzymatic browning reaction which occurs in the oral cavity results in the discoloration of teeth. Presently used anti-plaque agents accelerate this nonenzymatic browning reaction and further the staining of the teeth. Recently, a class of cationic anti-microbial agents with remarkable anti-plaque properties have been formulated in oral rinses for regular use to kill bacteria in the mouth. These agents, the cationic antiseptics, include such agents as alexidine, cetyl pyridinium chloride, chlorhexidine gluconate, hexetidine, and benzalkonium chloride.

Tooth staining by chlorhexidine and other anti-plaque agents apparently results from the enhancement of the Maillard reaction. Nordbo, *J. Dent. Res.*, 58, p. 1429 (1979) reported that chlorhexidine and benzalkonium chloride catalyze browning reactions in vitro. Chlorhexidine added to mixtures containing a sugar derivative and a source of amino groups underwent increased color formation, attributed to the Maillard reaction. It is also known that use of chlorhexidine results in an increased dental pellicle. Nordbo proposed that chlorhexidine resulted in tooth staining in two ways: first, by increasing formation of pellicle which contains more amino groups, and secondly, by catalysis of the Maillard reaction leading to colored products.

In accordance with this method, the compounds of Formula I are formulated into compositions adapted for use in the oral cavity. Particularly suitable formulations are oral rinses and toothpastes incorporating the active agent.

In the practice of this invention, conventional formulating techniques are utilized with nontoxic, pharmaceutically acceptable carriers typically utilized in the amounts and combinations that are well-known for the formulation of such oral rinses and toothpastes.

The agent of Formula I is formulated in compositions in an amount effective to inhibit the formation of advanced glycosylation endproducts. This amount will, of course, vary with the particular agent being utilized and the particular dosage form, but typically is in the range of 0.01% to 1.0%, by weight, of the particular formulation.

Additionally, since the agents of the aforesaid method are concentrated in the salivary glands upon oral ingestion or parenteral administration, they can be so administered. This concentration in the salivary glands results in their secretion into saliva, the net result being that they are functionally placed in the oral cavity where they can effect their desired method. For such administration, the particular agent can be formulated in any conventional oral or parenteral dosage form. A particularly desirable dosage form is the incorporation of the agent into a vitamin tablet or fluoride tablet so as to maximize patient, and particularly juvenile patient, compliance.

The compounds encompassed by Formula I are conveniently prepared by chemical syntheses well-known in the art. Certain of the compounds encompassed by Formula I are well-known compounds readily available from chemical supply houses and/or preparable by synthetic methods specifically published therefor. For instance, the following compounds are commercially available and/or described in the chemical and/or patent literature:

4-(cyclohexylamino-carbonyl)-o-phenylene diamine hydrochloride;
4-aminobenzhydrazide;
3,4-diaminobenzhydrazide;
4-(n-butylamino-carbonyl)-o-phenylene-diamine dihydrochloride;
4-(ethylamino-carbonyl)-o-phenylene-diamine dihydrochloride;
4-carbamoyl-o-phenylene diamine hydrochloride;
4-hydroxybenzhydrazide;
3-amino-4-hydroxybenzoic acid;
4-amino-3-hydroxybenzoic acid;
3-amino-4-hydroxybenzhydrazide;
3-amino-4-hydroxybenzhydrazide dihydrochloride;
4-amidinobenzamide hydrochloride;
2,4-diamino-3-hydroxybenzoic acid;
3,5-diamino-4-hydroxybenzoic acid;
4-amino-3-hydroxybenzoic acid;
4-amino-3-hydroxybenzamide;
4,5-diamino-2-hydroxybenzoic acid;
3,4-diaminobenzamide;
3,4-diaminobenzhydrazide;
3,4-diamino-N,N-bis(1-methylethyl)benzamide;
3,4-diamino-N,N-diethylbenzamide;
3,4-diamino-N,N-dipropylbenzamide;
3,4-diamino-N-(2-furanylmethyl)benzamide
3,4-diamino-N-(2-methylpropyl)benzamide;
3,4-diamino-N-(4,5-dihydro-2-thiazolyl)benzamide;
3,4-diamino-N-(5-methyl-2-thiazolyl)benzamide;
3,4-diamino-N-(6-methoxy-2-benzothiazolyl)benzamide;
3,4-diamino-N-(6-methoxy-8-quinolinyl)benzamide;
3,4-diamino-N-(6-methyl-2-pyridinyl)benzamide;
3,4-diamino-N-(1H-benzimidazol-2-yl)benzamide;
3,4-diamino-N-(2-pyridinyl)benzamide;
3,4-diamino-N-(2-thiazolyl)benzamide;
3,4-diamino-N-(4-pyridinyl)benzamide;
3,4-diamino-N-[9H-pyrido (3,4-b)indol-6-yl] benzamide;
3,4-diamino-N-butylbenzamide;
3,4-diamino-N-cyclohexylbenzamide;
3,4-diamino-N-cyclopentylbenzamide;
3,4-diamino-N-decylbenzamide;
3,4-diamino-N-dodecylbenzamide;
3,4-diamino-N-methylbenzamide;
3,4-diamino-N-octylbenzamide;
3,4-diamino-N-pentylbenzamide;
3,4-diamino-N-phenylbenzamide;
3-amino-4-hydroxybenzamide;
3-amino-4-hydroxy-N-octylbenzamide;
3,5-diamino-2-methylbenzoic acid;
5-aminoisophthalic acid;
3-aminophthalic acid hydrochloride;
3-hydroxyanthranilic acid;
3,5-diamino-4-methylbenzoic acid;

3-aminosalicylic acid;
4-aminosalicylic acid;
5-aminosalicylic acid;
4-guanidinobenzoic acid hydrochloride;
4,5-difluoroanthranilic acid;
4-fluoro-3-nitrobenzoic acid;
3-amino-2,5,6-trifluorobenzoic acid;
2-fluoro-5-nitrobenzoic acid;
3-amino-5-nitrosalicylic acid monohydrate;
2,4-dihydroxy-3,5-dinitrobenzoic acid;
3,5-dinitro-4-hydroxybenzoic acid;
methyl 3,5-dinitro-4-hydroxybenzoate;
3,5-dinitro-p-toluic acid;
3,5-dinitrosalicylic acid;
2-amino-3-methylbenzoic acid;
4-amino-3-methoxybenzoic acid;
2-amino-4,5-dimethoxybenzoic acid;
3,5-diaminobenzoic acid dihydrochloride;
2-aminoterephthalic acid;
3-amino-4-fluorobenzoic acid;
methyl 4-aminosalicylate;
4-aminosalicylhydrazide;
3,5-diamino-4-fluorobenzoic acid; and
5-aminosalicylic acid.

Certain of the compounds encompassed by Formula I are novel compounds, and, as such, are a further embodiment of the instant invention. These novel compounds are of the formula

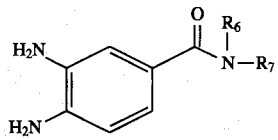
(IIa)

wherein $R_6$ is hydrogen and $R_7$ is a morpholino, piperidinyl, homopiperidinyl, or piperazinyl group; or, $R_6$ and $R_7$, together with the nitrogen atom, form a morpholino, piperidino, or piperazinyl group.

Representative compounds of Formula IIa are:
4-(morpholino-carbonyl)-o-phenylenediamine;
4-[(4-morpholino)hydrazino-carbonyl]-o-phenylenediamine;
4-(1-piperidinylamino-carbonyl)-o-phenylenediamine; and their pharmaceutically acceptable salts.

A still further group of novel compounds are those of the formula

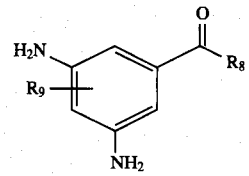
(IIb)

wherein $R_8$ is a hydroxy, alkoxy, hydrazino group, or a group of the formula $-NR_6R_7$
  wherein $R_6$ is hydrogen and $R_7$ is a morpholino, piperidinyl, homopiperidinyl, or piperazinyl group; or, $R_6$ and $R_7$, together with the nitrogen atom, form a morpholino, piperidino, or piperazinyl group; or when $R_6$ is hydrogen, then $R_7$ can also be a phenyl group;

$R_9$ is one or two hydroxy, alkoxy, lower alkylamino, diloweralkylamino or hydroxyloweralkylamino groups; with the proviso that when $R_8$ is a hydroxy group, then $R_9$ is a group other than hydroxy; and their pharmaceutically acceptable acid addition salts.

Representative compounds of Formula IIb are:

3,5-diamino-4-hydroxybenzoic acid;
3,5-diaminosalicylic acid;
methyl 3,5-diamino-4-hydroxybenzoate;
methyl 3,5-diamino-2,4-dihydroxybenzoate;
isopropyl 3,5-diamino-4-hydroxybenzoate;
4-(3,5-diamino-4-hydroxybenzoyl)morpholine;
ethyl 3,5-diamino-4-hydroxybenzoate;
isopropyl 3,5-diamino-2,4-dihydroxybenzoate;
3,5-diamino-4-hydroxybenzanilide;
ethyl 3,5-diamino-4-ethoxybenzoate;
isopropyl 3,5-diamino-4-isopropyloxybenzoate;
3,5-diamino-4-methoxybenzoic acid;
3,5-diamino-4-methoxybenzhydrazide;
methyl 3,5-diamino-4-methoxybenzoate;
3,5-diamino-4-methylaminobenzoic acid;
3,5-diamino-4-isopropylaminobenzoic acid;
3,5-diamino-4-dimethylaminobenzoic acid;
3,5-diamino-4-isopropyloxybenzhydrazide;
3,5-diamino-4-isopropyloxybenzoic acid;
3,5-diamino-4-hydroxyethylaminobenzoic acid;
and their pharmaceutically acceptable salts and hydrates.

The 4-(carbamoyl)- or 4-(substituted carbamoyl) orthophenylenediamines of Formula I wherein $R_1$ is an amino or $-NR_4R_5$ group can be prepared according to the reaction Scheme I below:

(Scheme I)

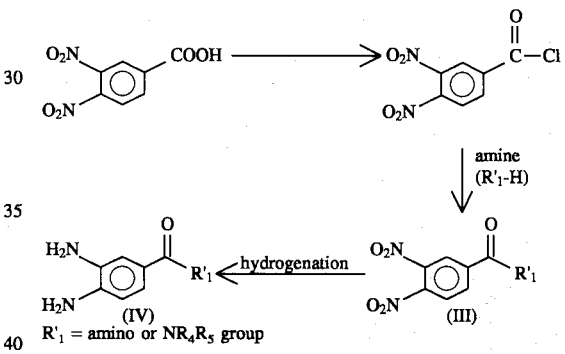

Typically, the 3,4-dinitrobenzoic acid starting material is dissolved in an aprotic solvent such as benzene or toluene and refluxed with thionylchloride for a period of about 2–6 hours to form the desired 3,4-dinitrobenzoyl chloride.

The 3,4-dinitrobenzoyl chloride is then purified to remove traces of starting materials, and then redissolved in an aprotic solvent such as benzene or methylene chloride. To this mixture is added the appropriate primary or secondary amine of the formula $R'_1$—H wherein $R'_1$ is an amino group or an $-NR_4R_5$ group, along with triethylamine, or another suitable acid acceptor. Typically, this reaction is completed in 4–24 hours at room temperature, thus affording a 4-carbamoyl or 4-substituted carbamoyl-1,2-dinitrobenzene of Formula III.

The 3,4-dinitrobenzamide of Formula III is then subjected to conventional hydrogenation procedures, for instance, hydrogen gas using a 10% palladium-on-carbon catalyst, typically, at 40–60 psi, and at room temperature for 12–24 hours. Thus produced is the desired 4-(carbamoyl)- or 4-(substituted carbamoyl)orthophenylene diamines of Formula IV.

Optionally, the compounds of Formula IV are isolated as their acid addition salts by conventional treatment thereof, with, for instance, hydrogen chloride, to produce the corresponding hydrochloride salt.

An alternate route for the preparation of the 4-(substituted carbamoyl)-o-phenylenediamines of Formula I wherein $R_1$ is an amino or —NR$_4$R$_5$ group involves the reaction Scheme II below.

Raney nickel. As noted hereinabove, the free base itself can be isolated, or, optionally, the corresponding acid addition Scheme (II)

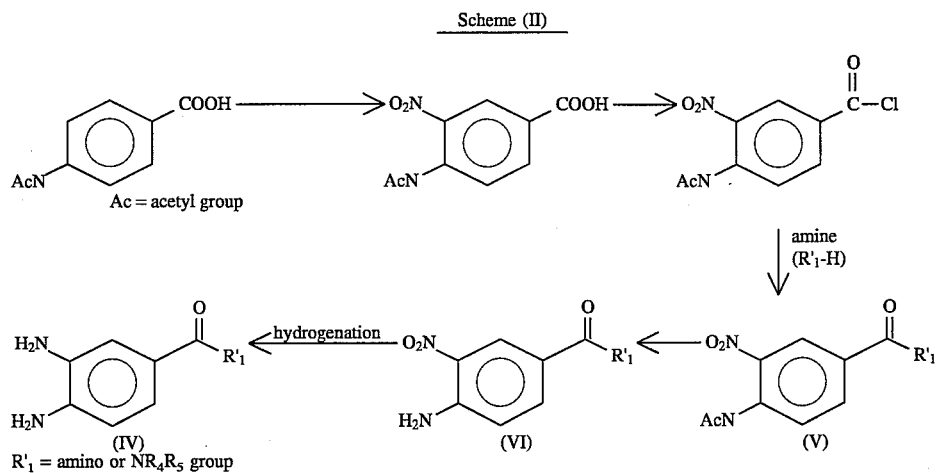

In this reaction sequence, partially described by Kumar et al., *J. Med. Chem.*, 27, pp. 1083–1089 (1984), 4-acetamidobenzoic acid is utilized as a starting material and is nitrated using, for instance, fuming nitric acid at about −10° to about 10° C. for 1–4 hours to afford 3-nitro-4-acetamidobenzoic acid. This compound is then reacted with thionyl chloride in a non-polar, aprotic solvent to afford the corresponding 3-nitro-4-acetamidobenzoyl chloride, which is then further reacted with the R'$_1$—H amine wherein R'$_1$ is an amino group or a —NR$_4$R$_5$ group, to afford the 3-nitro-4-acetamino compound of Formula V.

Hydrolysis of the 4-acetamino substituent of the compound of Formula V thus affords the corresponding amino group using, for instance, an aqueous ethanolic sodium hydroxide solution and a polar protic solvent as the reaction medium, to afford the 3-nitro-4-amino compound of Formula VI.

The 3-nitro substituent of the compound of Formula V is then reduced by standard hydrogenation techniques to afford the desired 4-(substituted carbamoyl)-o-phenylenediamine of Formula IV. Typically, Raney nickel is used as the catalyst in catalytic hydrogenation. Alternately, the 3-nitro substituent is reduced with hydrazine hydrate in the presence of salt can be generated by treatment with the appropriate acid prior to the final isolation step. This alternate reaction scheme involves somewhat milder hydrogenation conditions and may be preferable or afford higher yields for certain of the R'$_1$ substituents.

A further alternate route for the preparation of the 4-(substituted carbamoyl)-o-phenylenediamines of Formula I wherein R$_1$ is an amino or —NR$_4$R$_5$ group involves the reaction of methyl 3,4-diaminobenzoate with the R'$_1$—H amine. Typically, this reaction is conducted in a polar, porotic solvent such as methanol, at 1–2 atmospheres pressure. Reaction temperatures range from 60°–100° C., depending upon the solvent, and reaction times from about 12–48 hours. Again, the free base of Formula IV is produced, which can be isolated, or optionally treated, so as to afford the corresponding acid addition salt.

The 2-hydroxy-4-(substituted carbamoyl) or 2-hydroxy-5-(substituted-carbamoyl)-anilines of Formula I wherein R$_1$ is an amino or an —NR$_4$R$_5$ group can be prepared according to the reaction Scheme III below:

Scheme (III)

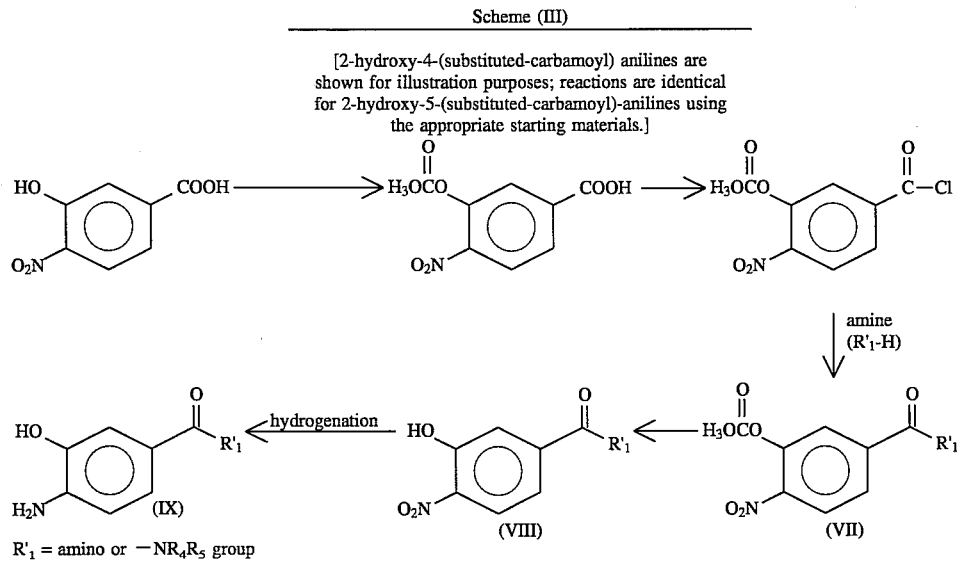

The 3-hydroxy-4-nitrobenzoic acid starting material is acetylated using, for instance, acetic anhydride and pyridine at reflux temperatures for 1–4 hours to afford 3-acetoxy-4-nitrobenzoic acid. This compound is then dissolved in a non-polar, aprotic solvent, such as benzene or toluene, and refluxed with thionyl chloride for a period of about 2–6 hours to form the desired 3-acetoxy-4-nitrobenzoyl chloride.

The 3-acetoxy-4-nitrobenzoyl chloride can then be optionally purified to remove traces of starting materials, or used directly, by redissolving it in an aprotic solvent such as methylene chloride. To this mixture is added the appropriate primary or secondary amine of the formula $R'_1$—H, wherein $R'_1$ is an amino or an —$NR_4R_5$ group, along with triethylene amine, or another suitable acid acceptor. Typically, this reaction is completed in 4–24 hours at room temperature, thus affording the 4-carbamoyl or 4-substituted-carbamoyl-1-nitro-2-hydroxybenzene of Formula VII.

Hydrolysis of the 3-acetoxy substituent of the compound of Formula VII, for instance, in an aqueous ethanolic sodium hydroxide solution and a polar protic solvent as the reaction medium, affords the 3-hydroxy-4-amino compound of Formula VIII.

The compound of Formula VIII is then subjected to conventional hydrogenation procedures, for instance, hydrogen gas using a 10% palladium-on-carbon catalyst at 40–60 psi, at room temperature for 12–36 hours. Thus afforded is the desired 2-hydroxy-4-(carbamoyl) or 4-(substituted carbamoyl)-anilines of Formula IX.

Optionally, these compounds of Formula IX can be isolated as their free bases, or alternately, as their acid addition salts. Typically, the acid addition salts are produced by treatment of the corresponding free base with the appropriate acid, e.g., hydrogen chloride, to afford the corresponding salt, e.g., hydrochloride.

The 3,5-diamino-4-substituted benzoic acids of the present invention represented by Formula XIIIa can be synthesized according to the reaction Scheme IV below:

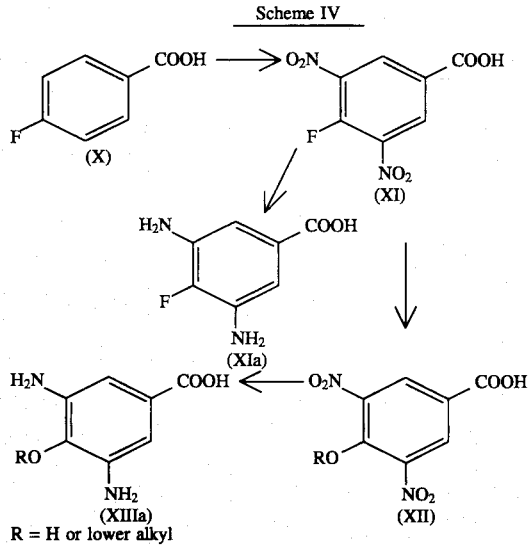

In this reaction scheme, 4-fluorobenzoic acid of Formula X is treated with fuming nitric acid to provide the 3,5-dinitro-4-fluorobenzoic acid of Formula XI. At this stage, the 4-fluoro substituent can be converted to a 4-alkoxy substituent by treatment with the appropriate alcohol or water and a base such as potassium hydroxide or sodium metal to yield the compound of Formula XII.

The compound of Formula XI or XII is then hydrogenated with $H_2$ gas, using a palladium-on-carbon or other similar catalyst, to give the 3,5-diamino-4-substituted compound of Formula XIIIa. Optional treatment of this compound of Formula XIIIa with a strong mineral acid such as hydrochloric acid provides the corresponding salts.

A variation of Scheme IV is utilized to produce the corresponding 2,3-diamino-4-substituted benzoic acids of Formula XIIIb which are position isomers. This variation utilizes 2-fluorobenzoic acid as a starting material, which is then reacted with nitric acid/sulfuric acid to produce the 5-fluoro-2-nitrobenzoic acid and subsequently hydrogenated and acetylated to produce 2-acetamido-5-fluoro-benzoic acid. Treatment of this compound with nitric acid/sulfuric acid affords the 2-acetamido-5-fluoro-3-nitrobenzoic acid which is deacylated and then hydrogenated to afford the 2,3-diamino-5-fluorobenzoic acid. In this variation, the hydroxylation or alkoxylation step can be performed on the nitro-substituted intermediate wherever necessary to afford the corresponding 2,3-diamino-4-substituted benzoic acids of the Formula XIIIb.

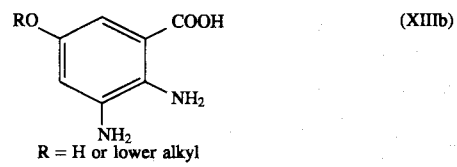

The 3,5-diamino-4-hydroxy-N-substituted benzamides of the present invention represented by formula XVII can be synthesized according to the reaction Scheme V below:

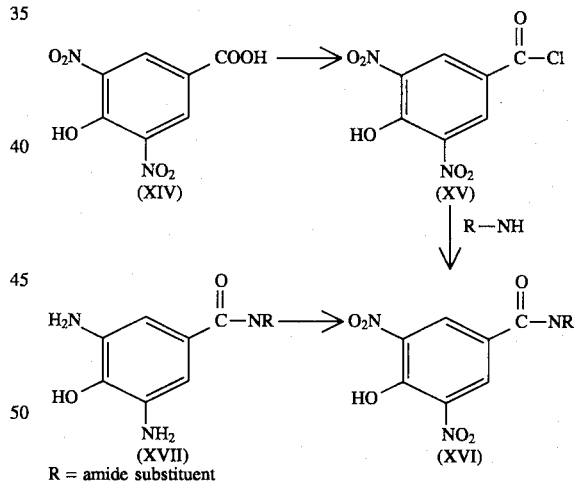

In this reaction scheme, 3,5-dinitro-4-hydroxybenzoic acid is treated with thionyl chloride to afford the corresponding acid chloride of Formula XV. Treatment of this acid chloride of Formula XV with the appropriate amine results in the 3,5-dinitro-4-hydroxybenzamide of Formula XVI. This compound of Formula XVI is then hydrogenated under conditions similar to those used in the Scheme IV hydrogenation step to yield the desired compounds of Formula XVII, which can optionally be converted to their acid addition salts by treatment with, for instance, HCl gas.

The 3,5-diamino-4-hydroxybenzoic acid esters of Formula XVII can be prepared by the following reaction Scheme VI below:

Scheme VI

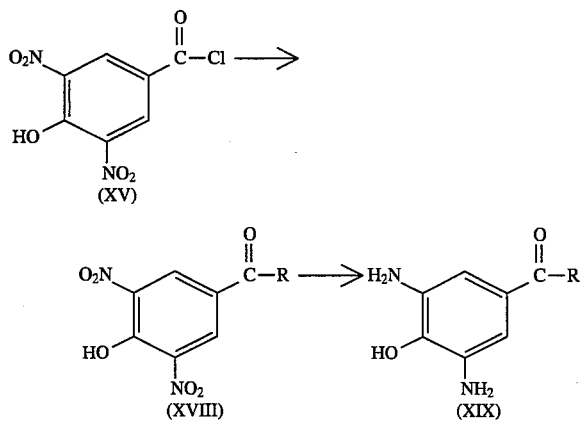

R = lower alkoxy

In this reaction sequence which begins with the compound of Formula XV prepared in Scheme V, the compound of Formula XV is treated with the appropriate alcohol and heated for periods of about 30 minutes to 2 hours to afford the desired compound of Formula XVI. This compound of Formula XV is then hydrogenated under conditions similar to those used in the Scheme IV hydrogenation stp to afford the desired compound of Formula XVII. Optionally, this compound can be treated appropriately to afford the corresponding acid addition salt.

EXAMPLE 1

The following method was used to evaluate the ability of the compounds of the present invention to inhibit glucose-mediated development of fluorescence of bovine serum albumin (BSA), a measure of cross-linking. Compounds were incubated under aseptic conditions at a concentration of 1 mM with 400 mM glucose and 100 mg/mL BSA in a 1.5M sodium phosphate buffer, pH 7.4.

Samples of the incubation mixture were taken immediately and after 1 week incubation at 37° C. for measurement of fluorescence. For each test compound, control incubations in buffer were made of compound alone (C), compound plus glucose (G+C), and compound plus BSA (B+C). An additional set of incubations of glucose and BSA (B+G) were prepared as the baseline controls against which were measured the ability of the compounds to inhibit. Each incubation was made in triplicate.

Fluorescence (excitation, 370 nm; emission, 440 nm) was measured on each sample after a 100-fold dilution in distilled water.

The % inhibition of browning of each test compound was calculated as follows. Each ΔF represents the fluorescence measurement of that sample after 1 week incubation less its fluorescence before incubation.

% inhibition =

$$\frac{\Delta F_{B+G} - [\Delta F_{B+G+C} - (\Delta F_C + \Delta F_{G+C} + \Delta F_{B+C})]}{\Delta F_{B+G}} \times 100$$

where B=BSA, G=glucose, and C=test compound.

Percent inhibition of browning by various test compounds at 1 mM:

0% no inhibitor;
66%  4-(butylamino-carbonyl)-o-phenylene-diamine dihydrochloride;
33% 4-carbamoyl-o-phenylene diamine hydrochloride;
66% 3-amino-4-hydroxybenzoic acid;
66% 3-amino-4-hydroxybenzhydrazide;
73%  4-(1-piperidinylamino-carbonyl)-o-phenylenediamine dihydrochloride.

The above experiments suggest that this type of drug therapy may have benefit in reducing the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints. This therapy might retard atherosclerosis and connective tissue changes that occur with diabetes and aging. Both topical, oral, and parenteral routes of administration to provide therapy locally and systemically are contemplated.

EXAMPLE 2

The following method was used to evaluate the ability of the compounds of the present invention to inhibit the cross-linking of glycated bovine serum albumin (AGE-BSA) to the rat tail tendon collagen coated 96-well plate.

The AGE-BSA was prepared by incubating BSA at a concentration of 200 mg per ml with 200 mM glucose in 0.4M sodium phosphate buffer, pH 7.4 at 37° C. for 12 weeks. The glycated BSA was then extensively dialyzed against phosphate buffer solution (PAS) for 48 hours with additional 5 times buffer exchanges. The rat tail tendon collagen coated plate was blocked first with 300 μl of superbloc blocking buffer (Pierce #37515X) for one hour. The blocking solution was removed from the wells by washing the plate twice with PAS-Tween 20 solution (0.05% Tween 20) using a NUNC-multiprobe or Dynatech ELISA-plate washer. Cross-linking of AGE-BSA (1 to 10 μg per well depending on the batch of AGE-BSA) to rat tail tendon collagen coated plate was performed with and without the testing compound dissolved in PAS buffer at pH 7.4 at the desired concentrations by the addition of 50 μl each of the AGE-BSA diluted in PAS or in the testing compound at 37° C. for 4 hours. The unbrowned BSA in PAS buffer with or without testing compound were added to the separate wells as the blanks. The un-cross-linked AGE-BSA was then removed by washing the wells three times with PAS-Tween buffer. The cross-linked AGE-BSA to the tail tendon coated plate was then quantitated by the polyclonal antibody raised against AGE-RNase. After a one-hour incubation period, AGE antibody was removed by washing 4 times with PAS-Tween.

The bound AGE antibody was then detected with the addition of horseradish peroxidase-conjugated secondary antibody—goat anti-rabbit immunoglobulin and incubation for 30 minutes. The substrate of 2,2-azino-di( 3-ethylbenzthiazoline sulfonic acid) (ABTS chromogen) (Zymed #00-2011) was added. The reaction was allowed for an additional 15 minutes and the absorbance was read at 410 nm in a Dynatech plate reader.

The % inhibition of each test compound was calculated as follows.

inhibition= {[Optical density (without compound)−optical density (with compound)]/optical density (without compound)]} 100%

The IC$_{50}$ relative inhibition by various test compounds at 10 Mm is as follows:

| Test Compound | Relative IC$_{50}$ (mM) |
|---|---|
| 3,5-diamino-4-hydroxybenzoic acid dihydrochloride | 0.09 ± 0.17 |
| 3,4,5-triaminobenzamide trihydrochloride | 2.90 ± 0.19 |
| 3,5-diaminosalicyclic acid hydrochloride | 0.18 ± 0.07 |
| 3-aminophthalic acid hydrochloride | 2.27 ± 0.17 |
| 3,5-diamino-4-methylbenzoic acid | 0.90 ± 0.13 |
| 3-aminosalicylic acid | 2.50 ± 0.13 |
| methyl 3,5-diamino-4-hydroxybenzoate dihydrochloride | 0.60 ± 0.13 |
| 3-amino-5-nitrosalicylic acid monohydrate | 0.63 ± 0.07 |
| ethyl 3,5-dinitro-4-hydroxybenzoate | 7.10 ± 0.03 |
| 2-amino-4,5-dimethoxybenzoic acid | 0.06 ± 0.22 |
| 3,5-diaminobenzoic acid dihydrochloride | 0.63 ± 0.20 |
| 2-aminoterephthalic acid | 2.80 ± 0.14 |
| methyl 3,5-diamino-2,4-dihydroxybenzoate | 0.17 ± 0.30 |
| 3-amino-4-fluorobenzoic acid | 0.80 ± 0.12 |
| isopropyl 3,5-diamino-4-hydroxybenzoate dihydrochloride | 0.12 ± 0.23 |
| methyl 4-aminosalicylate | 0.98 ± 0.22 |
| 4-aminosalicylhydrazide | 0.53 ± 0.15 |
| 4-(3,5-diamino-4-hydroxybenzoyl)morpholine monohydrochloride | 2.40 ± 0.07 |
| 3,5-diamino-4-fluorobenzoic acid | 8.00 ± 0.17 |
| ethyl 3,5-diamino-4-hydroxybenzoate dihydrochloride | 0.29 ± 0.26 |
| isopropyl 3,5-diamino-2,4-dihydroxybenzoate | 1.34 ± 0.27 |
| isopropyl 3,5-diamino-4-methylbenzoate | 9.90 ± 0.15 |
| ethyl 3,5-diamino-4-ethoxybenzoate | 8.50 ± 0.09 |
| isopropyl 3,5-diamino-4-isopropyloxybenzoate dihydrochloride | 2.90 ± 0.06 |
| 3,5-diamino-4-methoxybenzoic acid | 2.50 ± 0.18 |
| 3,5-diamino-4-methylbenzhydrazide | 1.40 ± 0.27 |
| 3,5-diamino-4-methoxybenzhydrazide | 2.30 ± 0.10 |
| isopropyl 3,4-diaminobenzoate monohydrochloride hemihydrate | 0.96 ± 0.18 |
| 3,4-diaminobenzohydroxamic acid | 1.21 ± 0.30 |
| 3,5-diamino-4-methylaminobenzoic acid dihydrochloride | 0.10 ± 0.10 |
| 3,5-diamino-4-isopropylaminobenzoic acid dihydrochloride monohydrate | 0.26 ± 0.17 |
| 3,5-diamino-4-dimethylaminobenzoic acid | 0.43 ± 0.16 |
| methyl 3-amino-4-fluorobenzoate | 0.94 ± 0.14 |
| 3,5-diamino-4-isopropyloxybenzhydrazide | 1.55 ± 0.12 |
| isopropyl 3-amino-4-hydrazinobenzoate | 1.30 ± 0.23 |
| 3-amino-4-fluorobenzhydrazide | 2.80 ± 0.19 |
| 3,5-diamino-4-isopropyloxybenzoic acid | 1.30 ± 0.13 |
| 3,5-diamino-4-hydroxyethylaminobenzoic acid | 0.53 ± 0.16 |
| 3-amino-4-fluorobenzhydrazide monohydrochloride | 2.29 ± 0.14 |
| 3,4,5-triaminobenzoic acid | 0.01 ± 0.28 |
| 2,3-diaminobenzoic acid | 0.04 ± 0.39 |
| 3,5-diamino-4-hydroxybenzoic acid dihydrochloride | 0.09 ± 0.17 |
| 3,4,5-triaminobenzamide trihydrochloride | 2.90 ± 0.19 |
| 3,5-diaminosalicylic acid hydrochloride | 0.18 ± 0.07 |
| 3,5-diamino-2-methylbenzoic acid | >10 |
| 4-aminoisophthalic acid | >10 |
| 5-aminophthalic acid hydrochloride | 2.27 ± 0.17 |
| 4-hydroxyanthranilic acid | >10 |
| 3,5-diamino-4-methyl benzoic acid | 0.90 ± 0.13 |
| 3,4-aminosalicylic acid | 2.50 ± 0.13 |
| 5-aminosalicylic acid | >10 |
| 3-aminosalicylic acid | >10 |
| 3-guanidinobenzoic acid hydrochloride | >10 |
| 4,5-difluoroanthranilic acid | >10 |
| 4-fluoro-3-nitrobenzoic acid | >10 |
| methyl 3,5-diamino-4-hydroxy benzoate dihydrochloride | 0.60 ± 0.13 |
| 3,5-dinitro-4-hydroxybenzoic acid | >10 |
| methyl 3,5-dinitro-4-hydroxybenzoate | >10 |
| ethyl 3,5-dinitro-4-hydroxybenzoate | 7.10 ± 0.03 |
| 3,5-dinitro-p-toluic acid | 10.9 ± 0.05 |
| 2-amino-3-methylbenzoic acid | >10 |
| 4-amino-3-methoxybenzoic acid | >10 |
| 2-amino-4,5-dimethoxybenzoic acid | 0.06 ± 0.22 |
| 3,5-diaminobenzoic acid dihydrochloride | 0.63 ± 0.20 |
| 2-aminoterephthalic acid | 2.80 ± 0.14 |
| methyl 3,5-diamino-2,4-dihydroxybenzoate | 0.17 ± 0.30 |
| 3-amino-4-fluorobenzoic acid dihydrochloride | 0.80 ± 0.12 |
| isopropyl-3,5-dinitro-4-hydroxybenzoate | 0.12 ± 0.23 |
| methyl 4-aminosalicylate | 0.98 ± 0.22 |
| 4-aminosalicylhydrazide | 0.53 ± 0.15 |
| 4-(3,5-diamino-4-hydroxybenzoyl)-morpholine monohydrochloride | 2.40 ± 0.07 |
| 3,5-diamino-4-fluorobenzoic acid | 8.00 ± 0.17 |
| ethyl 3,5-diamino-4-hydroxybenzoate dihydrochloride | 0.29 ± 0.26 |
| isopropyl 3,5-diamino-2,4-dihydroxybenzoate | 1.34 ± 0.27 |
| isopropyl 3,5-diamino-4-methylbenzoate | 9.90 ± 0.15 |
| ethyl 3,5-diamino-4-ethoxybenzoate | 8.50 ± 0.09 |
| isopropyl 3,5-diamino-4-isopropyloxybenzoate dihydrochloride | 2.90 ± 0.06 |
| 3,5-diamino-4-methoxybenzoic acid | 2.50 ± 0.18 |
| 3,5-diamino-4-methylbenzhydrazide | 1.40 ± 0.27 |
| 3,5-diamino-4-methoxybenzhydrazide | 2.30 ± 0.10 |
| isopropyl 3,4-diaminobenzoate monohydrochloride hemihydrate | 0.96 ± 0.18 |
| methyl 3-amino-4-hydrazinobenzoate | >10 |
| 5-aminosalicylic acid | >10 |
| 3,4-diaminobenzohydroxamic acid | 1.21 ± 0.30 |
| 3,5-diamino-4-methylaminobenzoic acid dihydrochloride | 0.10 ± 0.10 |
| 3,5-diamino-4-isopropylaminobenzoic acid dihydrochloride monohydrate | 0.26 ± 0.17 |
| 3,5-diamino-4-dimethylaminobenzoic acid | 0.43 ± 0.16 |
| methyl 3-amino-4-fluorobenzoate | 0.94 ± 0.14 |
| 3,5-diamino-4-isopropyloxybenzhydrazide | 1.55 ± 0.12 |
| isopropyl 3-amino-4-hydrazinobenzoate | 1.30 ± 0.23 |
| 3-amino-4-fluorobenzhydrazide | 2.80 ± 0.19 |
| 3-amino-4-fluorobenzhydrazide monohydrochloride | 2.29 ± 0.14 |
| 3,5-diamino-4-isopropyloxybenzoic acid | 1.30 ± 0.23 |
| 3,5-diamino-4-hydroxyethylaminobenzoic acid | 0.53 ± 0.16 |
| 3,4,5-triaminobenzoic acid | 0.01 ± 0.28 |
| 2,3-diaminobenzoic acid | 0.04 ± 0.39 |

The above experiments suggest that this type of drug therapy may have benefit in reducing the pathology associated with the advanced glycosylation of proteins and the formation of cross-links between proteins and other macromolecules. Drug therapy may be used to prevent the increased trapping and cross-linking of proteins that occurs in diabetes and aging which leads to sequelae such as retinal damage, and extra-vascularly, damage to tendons, ligaments and other joints. This therapy might retard atherosclerosis and connective tissue changes that occur with diabetes and aging. Both topical, oral, and parenteral routes of administration to provide therapy locally and systemically are contemplated.

EXAMPLE 3

| Tablet | mg/tablet |
|---|---|
| Compound of Formula I | 50 |
| Starch | 50 |
| Mannitol | 75 |
| Magnesium stearate | 2 |
| Stearic acid | 5 |

The compound, a portion of the starch and the lactose are combined and wet granulated with starch paste. The wet granulation is placed on trays and allowed to dry overnight at a temperature of 45° C. The dried granulation is comminuted in a comminutor to a particle size of approximately 20 mesh. Magnesium stearate, stearic acid and the balance of the starch are added and the entire mix blended prior to compression on a suitable tablet press. The tablets are compressed at a weight of 232 mg. using a $^{11}/_{32}$" punch with a hardness of 4 kg. These tablets will disintegrate within a half hour according to the method described in USP XVI.

EXAMPLE 4

| Lotion | mg/g |
|---|---|
| Compound of Formula I | 1.0 |
| Ethyl alcohol | 400.0 |
| Polyethylene glycol 400 | 300.0 |
| Hydroxypropyl cellulose | 5.0 |
| Propylene glycol | to make 1.0 g |

EXAMPLE 5

| Oral Rinse | |
|---|---|
| Compound of Formula I: | 1.4% |
| Chlorhexidine gluconate | 0.12% |
| Ethanol | 11.6% |
| Sodium saccharin | 0.15% |
| FD&C Blue No. 1 | 0.001% |
| Peppermint Oil | 0.5% |
| Glycerine | 10.0% |
| Tween 60 | 0.3% |
| Water to | 100% |

EXAMPLE 6

| Toothpaste | |
|---|---|
| Compound of Formula I: | 5.5% |
| Sorbitol, 70% in water | 25% |
| Sodium saccharin | 0.15% |
| Sodium lauryl sulfate | 1.75% |
| Carbopol 934, 6% dispersion in water | 15% |
| Oil of Spearmint | 1.0% |
| Sodium hydroxide, 50% in water | 0.76% |
| Dibasic calcium phosphate dihydrate | 45% |
| Water to | 100% |

EXAMPLE 7

To further study the ability of inhibitors of nonenzymatic browning to prevent the discoloration of protein on a surface, such as that which occurs on the tooth surface, the following surface browning experiment is performed. As a substitute for a pellicle-covered tooth surface, unexposed and developed photographic paper is used to provide a fixed protein (gelatin, i.e., collagen) surface on a paper backing. Five millimeter circles are punched and immersed for one week at 50° C. in a solution of 100 mM glucose-6-phosphate in a 0.5M phosphate buffer, pH 7.4, containing 3 mM sodium azide. Glucose-6-phosphate is a sugar capable of participating in nonenzymatic browning at a more rapid rate than glucose. In addition to the glucose-6-phosphate, chlorhexidine and/or a compound of Formula I are included. After incubation, the gelatin/paper disks are rinsed with water, observed for brown color, and photographed.

Incubation of the disks in glucose-6-phosphate alone shows slight brown color versus disks soaked in buffer alone. Inclusion of chlorhexidine (in the form of Peridex® at a final concentration of 0.04% chlorhexidine) shows significant browning. Addition of a compound of Formula I to the chlorhexidine completely inhibits browning of the gelatin, as does inclusion of a compound of Formula I in the absence of chlorhexidine.

The slight brown color formed by the action of glucose-6-phosphate on the gelatin surface alone and its prevention by a compound of Formula I demonstrates the utility of the present invention in preventing nonenzymatic browning of tooth surfaces. The enhanced browning in the presence of chlorhexidine and its prevention with a compound of Formula I demonstrates the utility of the present invention in preventing the anti-plaque agent-enhanced nonenzymatic browning which occurs with chlorhexidine.

EXAMPLE 8

General Procedure

A. Preparation of 4-(substituted-carbamoyl)-1,2-dinitrobenzenes (Compounds 1–8) of Formula III A mixture of 3,4-dinitrobenzoic acid (4.66 g, 22 mmole) dissolved in dry benzene (50 ml) and thionyl chloride (10 ml) was refluxed for 4 hours. The reaction mixture was then concentrated at reduced pressure, another aliquot (20 ml) of dry benzene was added, and the solution was then concentrated under reduced pressure to remove the traces of thionyl chloride. The same acid chloride was also prepared by using thionyl chloride (30 ml) and a few drops of dimethylformamide under the same reaction conditions.

The acid chloride was redissolved in dry benzene (30 ml) and to this was added, under stirring, the appropriate primary or secondary amine (22 mmole) in dry benzene (10 ml) and triethylamine (22 mmole) at room temperature. The reaction was continued at room temperature overnight. The solid separated was filtered and dried. It was purified by flash column chromatography (silica gel, 200–300 mesh, hexane: EtoAc 1:1) and crystallized from ethanol or DMF-$H_2O$. The physical data of compounds 1 to 7 are reported in Table 1, below.

The following amines of formula $R'_1$—H are used to prepare compounds 1 to 8, respectively:

(a) ammonia;
(b) ethylamine;
(c) butylamine;
(d) cyclohexylamine;
(e) morpholine;
(f) 4-aminomorpholine;
(g) 1-aminopiperidine; and
(h) hydrazine.

TABLE 1

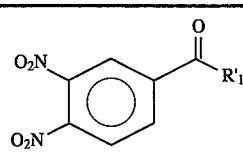

(III)

Physical Data of Compounds 1 to 8

| Compound | $R'_1$ | m.p. °C. | Yield % |
|---|---|---|---|
| 1 | —$NH_2$ | 137–138 | 60 |
| 2 | —$NHC_2H_5$ | 136–139 | 50 |
| 3 | —$NHC_4H_9$ | 75–76 | 30 |

TABLE 1-continued (III) structure: O₂N and O₂N substituted benzene with C(=O)R'₁

Physical Data of Compounds 1 to 8

| Compound | R'₁ | m.p. °C | Yield % |
|---|---|---|---|
| 4 | —NH—(cyclohexyl) | 130–131 | 53 |
| 5 | —N(morpholino) | 153–155 | 63 |
| 6 | —NH—N(morpholino) | 239–242 | 20 |
| 7 | —NH—N(piperidino) | 168–170 | 20 |
| 8 | —NHNH₂ | | |

Preparation of 4-(substituted-carbamoyl)-o-phenylenediamine hydrochlorides (Compounds 9 to 15) of formula IV A mixture of the appropriate 4-carboxamide-1,2-dinitrobenzene (compounds 1 to 8, 2 g) and 10% Pd/C (100 mg) in methanol (20 ml) was hydrogenated using hydrogen gas and 50 psi pressure at room temperature overnight. Filtration of the catalyst, followed by removal of the solvent under reduced pressure, yielded the desired diamino compound. It was converted as such into hydrochloride salt without further purification.

The diamine compound was dissolved in a minimum amount of methanol and the solution diluted with the same amount of ethyl acetate. The mixture was cooled to 0° C. and anhydrous hydrogen chloride gas was bubbled through the mixture for 15 minutes. The mixture was stored at −20° C. overnight. The solid separated was filtered and crystallized from a mixture of ethyl alcohol, water and ether. The physical data of compounds 8 to 15 are given in Table 2, below.

TABLE 2

(IV) structure: H₂N and H₂N substituted benzene with C(=O)R'₁

Physical Data of Compounds 9 to 16

| Compound | R'₁ | n° HCl | m.p. °C | Yield % |
|---|---|---|---|---|
| 9 | —NH₂ | 1 | 224–226 (dec) | 20 |
| 10 | —NHC₂H₅ | 2 | 228–230 | 48 |
| 11 | —NHC₄H₉ | 2 | 170–177 | 50 |

TABLE 2-continued (IV) structure: H₂N and H₂N substituted benzene with C(=O)R'₁

Physical Data of Compounds 9 to 16

| Compound | R'₁ | n° HCl | m.p. °C | Yield % |
|---|---|---|---|---|
| 12 | —NH—(cyclohexyl) | 1 | 266 | 50 |
| 13 | —N(morpholino) | 1 | 153–154 (dec) | 30 |
| 14 | —NH—N(morpholino) | 1 | 244–249 | 40 |
| 15 | —NH—N(piperidino) | 2 | 212–214 | 70 |
| 16 | —NHNH₂ | | 243–245 (dec) | 40 |

Similarly utilizing the following amines in the above-described synthetic procedure produces the corresponding 4-substituted carbamoyl orthophenylene diamine of formula IV:

| Amine (R'₁H) | Compound of Formula IV |
|---|---|
| diethyl amine | 4-(diethylamino-carbonyl)-o-phenylene diamine |
| tert-butylamine | 4-(tert-butylamino-carbonyl)-o-phenylene diamine |
| isobutylamine | 4-isobutylamino-carbonyl)-o-phenylene diamine |
| neopentylamine | 4-(neopentylamino-carbonyl)-o-phenylene diamine |
| dipropylamine | 4-(dipropylamino-carbonyl)-o-phenylene diamine |
| n-hexylamine | 4-(n-hexylamino-carbonyl)-o-phenylene diamine |
| n-decylamine | 4-(n-decylamino-carbonyl)-o-phenylene diamine |
| n-dodecylamine | 4-(n-dodecylamino-carbonyl)-o-phenylene diamine |
| 1-hexadecylamine | 4-(1-hexadecylamino-carbonyl)-o-phenylene diamine |
| octadecylamine | 4-(octadecylamino-carbonyl)-o-phenylene diamine |
| hydroxylamine | 4-(hydroxylamino-carbonyl)-o-phenylene diamine |
| ethanol amine | 4-(2-hydroxyethylamino-carbonyl)-o-phenylene diamine |
| 2-(2-aminoethylamine)ethanol | 4-[(2-hydroxyethylamino)ethylamino-carbonyl]-o-phenylene diamine |
| 2-(2-aminoethoxy)ethanol | 4-[(2-hydroxyethyloxy)ethylamino-carbonyl]-o-phenylene diamine |
| 6-amino-1-hexanol | 4-(6-hydroxyhexylamino-carbonyl)-o-phenylene diamine |
| 3-ethoxypropylamine | 4-(3-ethoxypropylamino-carbonyl)-o-phenylene diamine |

-continued

| Amine (R'₁H) | Compound of Formula IV |
|---|---|
| 3-isopropoxypropylamine | 4-(3-isopropoxypropylamino-carbonyl)-o-phenylene diamine |
| 3-dimethylaminopropylamine | 4-(3-dimethylaminopropylamino-carbonyl)-o-phenylene diamine |
| N,N,2,2-tetramethyl-1,3-propanediamine | 4-(N,N,2,2-tetramethyl-1,3-propanoamino-carbonyl)-o-phenylene diamine |
| 4-(2-aminoethyl)morpholine | 4-[4-(2-aminoethyl)morpholino-carbonyl]-o-phenylene diamine |
| 4-(3-aminopropyl)morpholine | 4-[4-(3-aminopropyl)morpholino-carbonyl]-o-phenylene diamine |
| N-(3-aminopropyl)pyrrolidine | 4-[N-(3-aminopropyl)pyrrolidino-carbonyl]-o-phenylene diamine |
| 1-amino-3-(N-piperidino)-propane | 4-[3-(N-piperidino)propylamino-carbonyl]-o-phenylene diamine |
| 1-(3-aminopropyl)-4-methyl-piperazine | 4-[3-(4-methylpiperazinyl)propyl-amino-carbonyl)-o-phenylene diamine |
| 1-(3-aminopropyl)imidazole | 4-(3-imidazoylpropylamino-carbonyl)-o-phenylene diamine |
| 3-phenyl-1-propylamine | 4-(3-phenylpropylamino-carbonyl)-o-phenylene diamine |
| N,N-diethylethylenediamine | 4-[2-(N,N-diethylamino)ethyl-amino-carbonyl]-o-phenylene diamine |
| 2-aminoimidazole | 4-(imidazolylamino-carbonyl)-o-phenylene diamine |
| pyrrolidine | 4-(pyrrolidinyl-carbonyl)-o-phenylene diamine |
| piperidine | 4-(piperidino-carbonyl)-o-phenylene diamine |
| 1-methylpiperazine | 4-(1-methylpiperazinyl-carbonyl)-o-phenylene diamine |
| 2,6-dimethylmorpholine | 4-(2,6-dimethylmorpholino-carbonyl)-o-phenylene diamine |
| 1-aminopyrrolidine | 4-(pyrrolidin-1-ylamino-carbonyl)-o-phenylene diamine |
| 1-aminohomopiperidine | 4-(homopiperidin-1-ylamino-carbonyl)-o-phenylene diamine |
| 1-amino-4-methylpiperazine | 4-(4-methylpiperazine-1-ylamino-carbonyl)-o-phenylene diamine |
| 4-amino-1,2,4-triazole | 4-(1,2,4-triazol-1-ylamino-carbonyl)-o-phenylene diamine |
| guanidine | 4-(guanidinyl-carbonyl)-o-phenylene diamine |
| aminoguanidine | 4-(guanidinylamino-carbonyl)-o-phenylene diamine |
| diaminoguanidine | 4-(aminoguanidinylamino-carbonyl)-o-phenylene diamine |
| triaminoguanidine | 4-(diaminoguanidinylamino-carbonyl)-o-phenylene diamine |

EXAMPLE 9

General Procedure

A. 3-acetoxy-4-(substituted carbamoyl)-1-nitrobenzenes (Compounds 17 to 22) of formula VII A mixture of 3-hydroxy-4-nitrobenzoic acid (10 g, 55 mmole) in acetic anhydride (20 ml) and anhydrous pyridine (20 ml) was refluxed for 4 hours. The reaction mixture was poured onto ice and the resulting mixture was extracted with ethyl acetate (2×100 ml). The organic layer was washed successively with dilute Hcl solution (2× 100 ml) and saturated brine solution, dried over $Na_2SO_4$, filtered and evaporated to give 3-acetoxy-4-nitrobenzoic acid.

A mixture of 3-acetoxy-4-nitrobenzoic acid (4.95 mg, 22 mmole) was taken up in thionyl chloride (30 ml) and a few drops of N,N-dimethylformamide was added. The reaction mixture was refluxed for 4 hours and concentrated at a reduced pressure. The acid chloride was used as such in the next step of the reaction.

The acid chloride was redissolved in dry methylene chloride (30 ml) and to this was added under stirring the appropriate amine ($R'_1$—H, 22 mmole) in dry methylene chloride (10 ml) and triethylamine (22 mmole) at room temperature. The reaction was continued at room temperature overnight. The solid separated was filtered and dried. It was purified by flash column chromatography (silica gel, 200–300 mesh, hexane: ethyl acetate (1:1)) and crystallized from ethanol or DMF-$H_2O$. The structures of compounds 17 to 22 are reported in Table 3, below.

The following amines are used to prepare compounds 17 to 22, respectively:

(a) ammonia;

(b) methyl hydrazine;

(c) 4-aminomorpholine;

(d) 1-aminopiperidine;

(e) 1-aminohomopiperidine; and (f) hydrazine.

TABLE 3

Structures of Compounds 17 to 22 (VII)

| Compound | $R'_1$ |
|---|---|
| 17 | —$NH_2$ |
| 18 | —HNNHMe |
| 19 | —HN—N(morpholino) |
| 20 | —HN—N(piperidino) |
| 21 | —HN—N(homopiperidino) |
| 22 | —HN—$NH_2$ |

B. 3-hydroxy-4-(substituted carbamoyl)-1-nitrobenzenes (Compounds 23 to 28) of formula VIII To a mixture of the appropriate 3-hydroxy-4-carboxamido- 1-nitrobenzene (compounds 17 to 22, 20 mmole) in ethanol (25 ml) was added sodium hydroxide solution (10%, 2 ml), and the mixture stirred at room temperature for 1 hour. This was followed by the addition of dilute HCl, and the precipitated compound was filtered, washed with water, dried, and recrystallized from ethanol or DMF-H$_2$O.

The structures of compounds 23 to 28 are given in Table 4, below.

TABLE 4

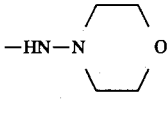

Structures of Compounds 23 to 28

| Compound | R'$_1$ |
|---|---|
| 23 | —NH$_2$ |
| 24 | —HNNHMe |
| 25 | —HN—N⌒O (morpholino) |
| 26 | —HN—N (piperidinyl) |
| 27 | —HN—N (homopiperidinyl) |
| 28 | —HN—NH$_2$ |

C. Preparation of 2-hydroxy-4-(substituted carbamoyl)-anilines (Compounds 29 to 34) of formula IX A mixture of the appropriate 3-hydroxy-4-carboxamido-nitrobenzene (compounds 23 to 28, 2 g) and 10% Pd/C (100 mg) in methanol (30 ml) was hydrogenated using hydrogen gas and 50 psi pressure at room temperature overnight. Filtration of the catalyst, followed by removal of the solvent under reduced pressure, yielded the desired amino compound. It was converted directly into hydrochloride salt without further purification.

The amino compound was dissolved in a minimum amount of methanol, cooled to 0° C. and anhydrous hydrogen chloride gas was bubbled through the mixture for 15 minutes. The mixture was stored at −20° C. overnight. The solid separated was filtered and crystallized from a mixture of ethyl alcohol, water and ether.

The structures of compounds 29 to 34 are given in Table 4, below. Thus produced are:

Compound 29: 2-hydroxy-4-(amino-carbonyl)aniline;

Compound 30: 2-hydroxy-4-(methylhydrazino-carbonyl) aniline;

Compound 31: 2-hydroxy-4-[1-(morpholino)amino-carbonyl] aniline;

Compound 32: 2-hydroxy-4[(1-piperidinyl)amino-carbonyl] aniline;

Compound 33: 2-hydroxy-4[(1-homopiperidinyl)amino-carbonyl] aniline;

Compound 34: 2-hydroxy-4-(hydrazinyl-carbonyl)aniline.

TABLE 5

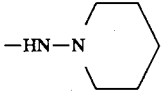

Structures of Compounds 29 to 34

| Compound | R'$_1$ |
|---|---|
| 29 | —NH$_2$ |
| 30 | —HNNHMe |
| 31 | —HN—N⌒O (morpholino) |
| 32 | —HN—N (piperidinyl) |
| 33 | —HN—N (homopiperidinyl) |
| 34 | —HN—NH$_2$ |

Similar utilization of the following amines in the above-described synthetic procedures produces the desired corresponding 2-hydroxy-4-(substituted carbamoyl)anilines of Formula IX.

| Amine | Compound of Formula IX |
|---|---|
| diethyl amine | 2-hydroxy-4-(diethylamino-carbonyl)aniline |
| tert-butylamine | 2-hydroxy-4-(tertbutylamino-carbonyl)aniline |
| isobutylamine | 2-hydroxy-4-(isobutylamino-carbonyl)aniline |
| neopentylamine | 2-hydroxy-4-(neopentylamino-carbonyl)aniline |
| dipropylamine | 2-hydroxy-4-(dipropylamino-carbonyl)aniline |
| n-hexylamine | 2-hydroxy-4-(n-hexylamino-carbonyl)aniline |
| n-decylamine | 2-hydroxy-4-(n-decylamino-carbonyl)aniline |
| n-dodecylamine | 2-hydroxy-4-(n-dodecylamino-carbonyl)aniline |
| 1-hexadecylamine | 2-hydroxy-4-(1-hexadecylamino-carbonyl)aniline |
| octadecylamine | 2-hydroxy-4-(octadecylamino-carbonyl)aniline |
| hydroxylamine | 2-hydroxy-4-(hydroxylamino-carbonyl)aniline |
| ethanol amine | 2-hydroxy-4-(2-hydroxyethyl-amino-carbonyl)aniline |
| 2-(2-aminoethylamine)ethanol | 2-hydroxy-4-((2-hydroxyethyl-amino)ethylamino-carbonyl)aniline |
| 2-(2-aminoethoxy)ethanol | 2-hydroxy-4-((2-hydroxyethyl-oxy)ethylamino-carbonyl)aniline |
| 6-amino-1-hexanol | 2-hydroxy-4-(6-hydroxyhexyl-amino-carbonyl)aniline |
| 3-ethoxypropylamine | 2-hydroxy-4-(3-ethoxypropyl amino-carbonyl)aniline |
| 3-isopropoxypropylamine | 2-hydroxy-4-(3-isopropoxypropyl-amino-carbonyl)aniline |

-continued

| Amine | Compound of Formula IX |
|---|---|
| 3-dimethylaminopropylamine | 2-hydroxy-4-(3-dimethylamino-propyl amino-carbonyl)aniline |
| N,N,2,2-tetramethyl-1,3-propanediamine | 2-hydroxy-4-(N,N,2,2-tetra-methyl-1,3-propanoamino-carbonyl) aniline |
| 4-(2-aminoethyl)morpholine | 2-hydroxy-4-(4-(2-amino-ethyl)morpholino-carbonyl)-aniline |
| 4-(3-aminopropyl)morpholine | 2-hydroxy-4-[4-(3-aminopropyl)-morpholino-carbonyl]aniline |
| N-(3-aminopropyl)pyrrolidine | 2-hydroxy-4-[N-(3-aminopropyl)-pyrrolidino-carbonyl]aniline |
| 1-amino-3-(N-piperidino) propane | 2-hydroxy-4-[3-(N-piperidino)-propylamino-carbonyl]aniline |
| 1-(3-aminopropyl)-4-methyl-piperazine | 2-hydroxy-4-[3-(4-methylpiper-azinyl)propylamino-carbonyl] aniline |
| 1-(3-aminopropyl)imidazole | 2-hydroxy-4-(3-imidazoylpropyl-amino-carbonyl)aniline |
| 3-phenyl-1-propylamine | 2-hydroxy-4-(3-phenylpropyl-amino-carbonyl)aniline |
| N,N-diethylethylenediamine | 2-hydroxy-4-[2-(N,N-diethyl-amino)ethylamino-carbonyl] aniline |
| 2-aminoimidazole | 2-hydroxy-4-(imidazolylamino-carbonyl)aniline |
| pyrrolidine | 2-hydroxy-4-(pyrrolidinyl-carbonyl)aniline |
| piperidine | 2-hydroxy-4-(piperidino-carbonyl)aniline |
| 1-methylpiperazine | 2-hydroxy-4-(1-methylpiper-azinyl-carbonyl)aniline |
| 2,6-dimethylmorpholine | 2-hydroxy-4-(2,6-dimethylmorph-olino-carbonyl)aniline |
| 1-aminopyrrolidine | 2-hydroxy-4-(pyrrolidin-1-yl-amino-carbonyl)aniline |
| 1-aminohomopiperidine | 2-hydroxy-4-(homopiperidin-1-ylamino-carbonyl)aniline |
| 1-amino-4-methylpiperazine | 2-hydroxy-4-(4-methylpiperazine-1-ylamino-carbonyl)aniline |
| 4-amino-1,2,4-triazole | 2-hydroxy-4-(1,2,4-triazol-1-ylamino-carbonyl)aniline |
| guanidine | 2-hydroxy-4-(guanidinyl-carbonyl)aniline |
| aminoguanidine | 2-hydroxy-4-(guanidinylamino-carbonyl)aniline |
| diaminoguanidine | 2-hydroxy-4-(aminoguanidinyl-amino-carbonyl)aniline |
| triaminoguanidine | 2-hydroxy-4-(diaminoguanidinyl-amino-carbonyl)aniline |

EXAMPLE 10

3,5-Diamino-4-Hydroxybenzoic Acid Dihydrochloride

A. 3,5-Dinitro-4-hydroxybenzoic acid (Aldrich) (4.56 g, 20 mmole) was dissolved in glacial acetic acid (25ml) and 10% Pd/C (15 mg) was added. The mixture was hydrogenated under hydrogen gas at 60 psi at 60° C. for 4 hours. It was then filtered through a celit pad and evaporated to dryness. The residue was crystallized from water to give 3,5-diamino-4-hydroxybenzoic acid (2.35g, 70%), m.p. 205° C. (lit ref., Simandi et al., Hungarian Patent 53602-A 2-901128 (1990), m.p. 205° C.).

B. 3,5-Diamino-4-hydroxybenzoic acid (2 g, 11.9 mmole) was dissolved in 6N hydrochloric acid (50 ml) and refluxed for 2 hours. The mixture was evaporated to dryness and the residue was treated with ethyl acetate (50 ml), filtered and dried to give 3,5-diamino-4-hydroxybenzoic acid dihydrochloride (2.58 g, 90%), m.p. 260°–262° C. (dec.) (lit. ref., Chemical Abstracts, 1908, 2379, m.p. 260° C. (dec)).

EXAMPLE 11

3,5-Dinitro-4-Fluorobenzoic Acid

This compound was prepared by the procedure of Nielsen et al. *J. Org. Chem.*, 1984, 24, 4575.

4-Fluorobenzoic acid (Aldrich, 14 g, 10 mmole) was added, with stirring, during 10 min. to a mixture of oleum (30% 50 g, 69 ml) and 90% nitric acid (56 ml) keeping the temperature below 25° C. by ice-bath cooling. The resulting clear yellow solution was heated to 85° C. during 10 min. (reflux condenser attached); the heating bath was then removed, after the initial exotherm had subsided, the reaction flask was then heated at 95° C., while stirring, for 3 hours. The mixture was then cooled and poured onto ice. Filtration, and washing with water, gave 17.25 g (74.8) of the title compound m.p. 238°–240° C. (Lit. ref. Nielsen et al., *J. Org. Chem.*, (1984), 24, 4575, m.p. 235°–237° C.)

3.5-Diamino-4-Fluorobenzoic Acid

A mixture of 3,5-dinitro-4-fluorobenzoic Acid (2 g, 8.69 mmole) and 10% Pd/C (100 mg) in methanol (50 ml) was hydrogenated using hydrogen gas and 50 psi pressure at room temperature overnight. Filtration of the catalyst, followed by removal of the solvent under reduced pressure yielded the title diamino compound (1.12 g, 75.7%) m.p. 213°–215° C.

EXAMPLE 12

3,5-Diamino-4-methoxybenzoic Acid

A. 3,5-Dinitro-4-methoxybenzoic Acid

This compound was prepared according to the procedure described by Goldstein et al., *Helv. Chimica. Acta*, 1954, 37, 2083.

3,5-Dinitro-4-fluorobenzoic acid (2, 2 g, 8.26 mmole) was dissolved in absolute methanol (40 ml) and 6% methanolic potassium hydroxide (20 ml) was added to the reaction. The mixture was stirred at room temperature for 30 minutes. The reaction mixture was acidified with conc. hydrochloric acid and evaporated to dryness. The residue was crystallized from aqueous methanol to yield 1.99 g (82.2%, m.p. 178°–179° C. (Lit. m.p. 178° C.).

B. 3,5-Diamino-4-methoxybenzoic Acid

A mixture of 3,5-dinitro-4-methoxybenzoic acid (2 g, 8.26 mmole) was reduced by hydrogenation, using the same procedure described in Example 10, to give 3,5-diamino-4-methoxybenzoic acid in 76.6% yield, m.p. 218°–220 ° C. (dec.)

Using the above-described procedure, the corresponding 3,5-diamino-4-substituted benzoic acids of formula III are prepared from the appropriate starting alcohols:

| Starting Alcohol | Compound of Formula XIII |
|---|---|
| Ethyl Alcohol | 3,5-diamino-4-ethoxybenzoic acid |
| Propyl Alcohol | 3,5-diamino-4-n-propoxybenzoic acid |
| Butyl Alcohol | 3,5-diamino-4-n-butoxybenzoic acid |
| Isopropyl Alcohol | 3,5-diamino-4-isopropoxybenzoic acid |
| Isobutyl Alcohol | 3,5-diamino-4-isopropoxybenzoic acid |
| Ethylene Glycol | 3,5-diamino-4-(2-hydroxyethoxy)benzoic acid |
| Methyl Glycolate | 3,5-diamino-4-methoxycarbonylmethoxy-benzoic acid |
| N-Benzylethanolamine | 3,5-diamino-4-[2-(N-benzylamino) ethoxy]-benzoic acid |

| Starting Alcohol | Compound of Formula XIII |
|---|---|
| Ethanolamine | 3,5-diamino-4-(2-amino)ethoxybenzoic acid |

EXAMPLE 13

General Procedure for the Preparation of
3,5-Dinitro-4-Hydroxy-N-Substituted Benzamides
(Compounds of 35–40 of Table 6)

3,5-Dinitro-4-hydroxybenzoic acid (4.56 g, 20 mmole) was taken up in thionyl chloride (40 ml) and refluxed for 4 hours. The thionylchloride was then removed by distillation under reduced pressure to give the crude acid chloride which was used as such in the next step of the reaction.

The acid chloride was redissolved in dry benzene (100 ml) and to this was added, under stirring, the excess of the appropriate amine (10 ml). The reaction mixture was then refluxed for 3 hours and stirred at room temperature overnight. The solid separated, was filtered and dried. It was crystallized from ethanol or DMF.H$_2$O. The physical data of compounds 35 to 40 is reported in Table 6.

The following starting amines are used to prepare compound 35 to 40, respectively:

(a) Morpholine;
(b) Diethyl Amine;
(c) Cyclopropylamine;
(d) Cyclohexylamine;
(e) Aniline; and
(f) 4-Amino Morpholine.

TABLE 6

Physical Data of Compounds of Formula XVI

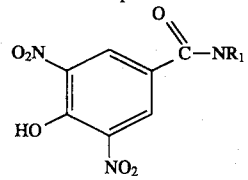

| Compound | R$_1$ | M.P. °C. | Yield % |
|---|---|---|---|
| 35 | —N(morpholine) | 164–166 | 85 |
| 36 | —N(C$_2$H$_5$)$_2$ | 166–168 | 93 |
| 37 | —NH—(cyclopropyl) | 168–171 (dec) | 90 |
| 38 | —NH—(cyclohexyl) | 162–163 | 97 |
| 39 | —NH—(phenyl) | 219–221 (dec) | 95 |

TABLE 6-continued

Physical Data of Compounds of Formula XVI

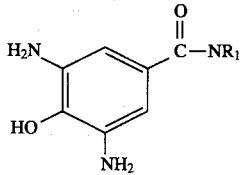

| Compound | R$_1$ | M.P. °C. | Yield % |
|---|---|---|---|
| 40 | —NH—N(morpholine) | 174–177 (dec) | 79 |

EXAMPLE 14

General Procedure for the Preparation of
3,5-Diamino-4-Hydroxy-N-Substituted Benzamide Hydrochlorides A mixture of the appropriate 3,5-dinitro-4-hydroxy-N-substituted benzamide (compounds 35–40), 2 g and 10% Pd/c (100 mg) in methanol (50 ml) was hydrogenated using hydrogen gas and 50 psi pressure at room temperature overnight. Filtration of the catalyst, followed by removal of the solvent under reduced pressure yielded the desired diamino compound. It was converted as such into hydrochloride salt without further purification.

The diamino compound was dissolved in minimum amount of methanol and the solution cooled to 0° C. Anhydrous hydrogen chloride gas was then bubbled through the mixture for 15 minutes. The mixture was stored at –20° C. overnight whereupon the solid separated. Filtration of the solid and recrystallization from a mixture of ethyl alcohol, water and ether affords the desired hydrochloride salt.

The physical data of the resultant compounds 41–46 is given in Table 7.

TABLE 7

Physical Data of Compounds of Formula XVII

| Compound | R$_1$ | N | M.P. °C. | Yield % |
|---|---|---|---|---|
| 41 | —N(morpholine) | 2 | 238–240 | 40 |

Utilizing compound 35, 4-(3,5-diamino-4-hydroxybenzoyl)morpholine hydrochloride, m.p. 238°–240 ° C. is produced.

Utilizing compound 36, 3,5-diamino-4-hydroxy-N,N-diethylbenzamide is produced.

Utilizing compound 37, 3,5-diamino-4-hydroxy-N-cyclopropylbenzamide is produced.

Utilizing compound 38, 3,5-diamino-4-hydroxy-N-cyclohexylbenzamide is produced.

Utilizing compound 39, 3,5-diamino-4-hydroxy-N-phenylbenzamide is produced.

Utilizing compound 40, 3,5-diamino-4-hydroxy-N-morpholinobenzamide (compound 46) is produced.

Using the appropriate starting amines, the following 3,5-diamino-4-hydroxy-N-substituted benzamides of formula XII are synthesized by the procedures described in Examples 13 and 14 hereinabove:

| Starting Amine | Compound of Formula XII |
|---|---|
| ammonia | 3,5-diamino-4-hydroxybenzamide |
| methyl amine | 3,5-diamino-4-hydroxy-N-methylbenzamide |
| ethyl amine | 3,5-diamino-4-hydroxy-N-ethylbenzamide |
| propyl amine | 3,5-diamino-4-hydroxy-N-propylbenzamide |
| butyl amine | 3,5-diamino-4-hydroxy-hydroxy-N-butyl-benzamide |
| dimethyl amine | 3,5-diamino-4-hydroxy-N,N-dimethyl-benzamide |
| tert-butyl amine | 3,5-diamino-4-hydroxy-N,N-t-butyl-benzamide |
| isobutylamine | 3,5-diamino-4-hydroxy-N-iso-butyl-benzamide |
| neopentylamine | 3,5-diamino-4-hydroxy-N-neo-pentyl-benzamide |
| dipropylamine | 3,5-diamino-4-hydroxy-N,N-dipropyl-benzamide |
| hexylamine | 3,5-diamino-4-hydroxy-N-hexylbenzamide |
| decylamine | 3,5-diamino-4-hydroxy-N-decylbenzamide |
| dodecylamine | 3,5-diamino-4-hydroxy-N-dodecyl-benzamide |
| 1-hexadecylamine | 3,5-diamino-4-hydroxy-N-(1-hexadecyl)-benzamide |
| octadecylamine | 3,5-diamino-4-hydroxy-N-octadecyl-benzamide |
| hydroxylamine | 3,5-diamino-4-hydroxy N-hydroxyl-benzamide |
| ethanolamine | 3,5-diamino-4-hydroxybenzohydroxamic acid |
| 6-amino-1-hexanol | 3,5-diamino-4-hydroxy-N-(6-hydroxy-hexyl)benzamide |
| 3-ethoxypropyl-amine | 3,5-diamino-4-hydroxy-N-(3-ethoxy-propyl)benzamide |
| 3-isopropoxypropyl-amine | 3,5-diamino-4-hydroxy-N-(3-isopropoxypropyl)benzamide |
| 4-(2-aminoethyl)-morpholine | 3,5-diamino-4-hydroxy-N-[4-(2-ethyl)morpholino]-benzamide |
| 4-(3-aminopropyl)-morpholine | 3,5-diamino-4-hydroxy-N-[4-(3-propyl)-morpholino]-benzamide |
| N-(3-aminopropyl)-pyrrolidine | 3,5-diamino-4-hydroxy-N-[N-(3-propyl)-pyrrolidinyl]-benzamide |
| 2-aminoimidazole | 3,5-diamino-4-hydroxy-N-imidazolyl-benzamide |
| 1-aminopyrrolidine | 3,5-diamino-4-hydroxy-N-pyrrolidinyl-benzamide |
| 1-aminopiperidine | 3,5-diamino-4-hydroxy-N-piperidinyl-benzamide |
| 1-aminohomopiper-idine | 3,5-diamino-4-hydroxy-N-homopiperidinyl-benzamide |
| 1-amino-4-methyl-piperazine | 3,5-diamino-4-hydroxy-N-(4-methylpiperazinylbenzamide |

EXAMPLE 15

Methyl 3,5-Dinitro-4-Hydroxybenzoate Dihydrochloride

A. Methyl 3,5-Dinitro-4-Hydroxybenzoate 3,5-dinitro-4-hydroxybenzoic acid (4.56 g 20 mmole) was taken up in thionyl chloride (40 ml) and refluxed for 4 hours. The thionyl chloride was then removed by distillation under reduced pressure to give the crude acid chloride which was used without further purification in the next step of the reaction.

The crude acid chloride was redissolved in dry methanol (50 ml) and refluxed for 1 hour. The reaction mixture was stored at –20° C. overnight whereupon the solid separated. This solid was filtered, dried and recrystallized from methanol to yield the desired product, 4.00 g (83%), m.p. 110°–115° C.

B. Methyl 3,5-diamino-4-hydroxybenzoate Dihydrochloride

Methyl 3,5-dinitro-4-hydroxybenzoate (prepared as in Step A, 3 g, 12.39 mmole) was hydrogenated using the same procedure described in Example 10 to yield methyl 3,5-diamino-4-hydroxybenzoate. It was purified by flash column chromatography (silica gel ethyl acetate) and used without further purification in the next step of the reaction.

The resultant ester was dissolved in minimum amount of methanol and cooled to 0° C. Dry hydrogen chloride gas was passed through the mixture for 15 minutes. After storing –20° C. overnight, the separated solid was filtered and dried. It was crystallized from ethanol, water and ether to give the desired compound 1.80 g (57%), m.p. 251– 252.

EXAMPLE 16

Isopropyl 3,5-diamino-4-hydroxybenzoate Dihydrochloride

A. Isopropyl 3,5-dinitro-4-hydroxybenzoate 3,5-dinitro-4-hydroxybenzoic acid (4.56 g, 20 mmole) was taken up in thionyl chloride (40 ml) and refluxed for 4 hours. Thionyl chloride was then removed by distillation under reduced pressure to give the crude acid chloride which was used without further purification in the next step of the reaction.

The crude acid chloride was redissolved in dry isopropanol (50 ml) and refluxed for 1 hour. The reaction mixture was stored at –20° C. overnight whereupon the solid which separated was filtered and dried to give the title product. Yield: 5.38 g (99%), m.p. 108°–110° C.

B. Isopropyl 3,5-diamino-4-hydroxybenzoate Dihydrochloride

Isopropyl 3,5-dinitro-4-hydroxybenzoate, 3 g, 11.02 mmole was hydrogenated using the same procedure described in Example 10 to yield isopropyl 3,5-diamino-4-hydroxybenzoate. It was purified by flash column chromatography (silica gel, ethyl acetate) and used without further purification in the next step of the reaction.

The ester was dissolved in minimum amount of methanol and cooled to 0° C. Dry hydrogen chloride gas was passed through the mixture for 15 minutes. It was stored at –20 ° C. overnight, whereupon the solid which separated was filtered and dried. It was crystallized from ethanol, water and ether mixture to give 1.66 g of the title product (53%), m.p. 247°–249° C.

Using the appropriate starting alcohol, the following 3,5-diamino-4-substituted benzoic acid esters of Formula XXII are produced:

| Starting Alcohol | Compound of Formula XXIV | M.P. °C. |
|---|---|---|
| ethyl alcohol | ethyl 3,5-diamino-4-hydroxy-benzoate dihydrochloride | 223–224 |
| propyl alcohol | n-propyl 3,5-diamino-4-hydroxybenzoate | |
| butyl alcohol | n-butyl 3,5-diamino-4-hydroxy-benzoate | |
| isopropyl alcohol | isopropyl 3,5-diamino-4-hy- | |

| Starting Alcohol | Compound of Formula XXIV | M.P. °C. |
| --- | --- | --- |
| | droxybenzoate | |
| Isobutyl alcohol | isobutyl 3,5-diamino-4-hydroxy-benzoate | |
| ethylene glycol | 2-hydroxyethyl 3,5-diamino-4-hydroxybenzoate | |
| methyl glycolate | methoxycarbonylmethyl 3,5-diamino-4-hydroxybenzoate | |
| N-benzylethanolamine | 2-(N-benzylamino)ethyl 3,5-diamino-4-hydroxybenzoate | |
| ethanolamine | 2-aminoethyl 3,5-diamino-4-hydroxybenzoate | |

EXAMPLE 17

2,3-Diamino-5-Fluorobenzoic Acid

A. 5-Fluoro-2-Nitrobenzoic Acid

Fuming nitric acid (6.0 mL) was added to concentrated sulfuric acid (60 mL) at 0° C. and stirred for several minutes. To this solution was added 3-fluorobenzoic acid (5.60 g, 40 mmol) over 30 minutes and the reaction was allowed to continue for another 6 hours in an ice bath. The reaction was poured onto cracked ice, and the precipitate was collected by filtration and dried to give 5-fluoro-2-nitrobenzoic acid (7.20 g, 97%) as a white solid.: m.p. 118°–120°; 1H NMR (400 MH$_z$, DMSO-d6) δ 7.62 (dt, 1H), 7.71 (dd, 1H), 8.14 (dd, 1H); 13C NMR (100 MH$_z$, DMSO-d6) δ 117.1, 117.4, 119.2, 119.5, 127.6, 127.7, 131.5, 131.6, 144.5, 162.9, 165.4, 165.6.

B. 2-Amino-5-Fluorobenzoic Acid

To a pressure flask capable of withstanding, 150 psi. was added 5-fluor-2-nitrobenzoic acid (2.0 g, 0.01 1 mol) dissolved in ethanol (40 mL) and 10% palladium on carbon (200 mg). The reaction was placed in a Parr apparatus and the flask flushed three times with hydrogen leaving an internal pressure of 65 psi. The reaction was continued for 16 hours while maintaining a pressure of 65 psi. The reaction was filtered through celite, washed with ethanol and the filtrate evaporated to dryness to give 2-amino-5-fluorobenzoic acid (1.22 g, 73%) as an off-white solid.: m.p. 183°–184°; 1H NMR (400 MH$_z$, DMSO-d6) δ 6.75 (dd, 1H), 7.16 (dt, 1H), 7.36 (dd, 1H); 13C NMR (100 MH$_z$, DMSO-d6) δ 109.3, 109.4, 115.4, 115.6, 117.8, 117.9, 121.5, 121.9, 148.3, 150.8, 153.8, 168.6, 168.7.

C. 2-Acetamido-5-Fluorobenzoic Acid

To a flask containing acetic anhydride (60 mL) was slowly added 2-amino-5-fluorobenzoic acid (7.68 g, 0.05 mol) over 20 minutes and continued to stir over 2 hours at room temperature. The product was collected by filtration and allowed to dry to give 2-acetamido-5-fluorobenzoic acid (8.03 g, 82) as an off white solid.: m.p. 168°–170°; 1H NMR (400 MH$_z$, DMSO-d6) δ 2.11 (s, 3H), 7.46 (dt, 1H), 7.65 (dd, 1H), 8.41 (dd, 1H), 10.83 (s, 1H); 13C NMR (100 MH$_z$, DMSO-d6) δ 25.3, 117.1, 117.4, 119.3, 121.2, 121.4, 122.9, 137.6, 156.0, 158.4, 168.7, 168.9.

D. 2-Acetamido-5-fluoro-3-nitrobenzoic acid

Fuming nitric acid (2.0 mL) was added to concentrated sulfuric acid (14 mL) at 0° C. 2-acetamido-5-fluoro-3nitrobenzoic acid (4.0 g, 0.02 mol) was slowly added to this solution over one hour while maintaining a temperature of 0° C. After one hour, the solution was warmed to room temperature and stirring was continued for another 3 hours. The reaction was poured onto cracked ice (250 g) and the precipitate collected by filtration and washed with water. The precipitate was dried and light yellow solid of 2-acetamido-5-fluoro-3-nitrobenzoic acid (4.32 g, 88%) was obtained.: m.p. 169°–171° (dec); 1H NMR (400 MH$_z$, DMSO-d6) δ 2.02 (s,3H), 7.95 (dd, 1H), 8.11 (dd, 1H), 10.22 (s, 1H); 13C NMR (100 MH$_z$, DMSO-d6) δ 23.5, 115.9, 116.2, 121.7, 121.9, 127.1, 131.0, 131.1, 146.9, 147.0, 156.5, 159.0, 166.0, 169.4.

E. 2-Amino-5-Fluoro-3-Nitrobenzoic Acid

Method A: 2-Acetamido-5-fluoro-3-nitrobenzoic acid (200 mg, 0.83 mmol) was added to 3N hydrochloric acid (4.0 mL) and the solution allowed to reflux for 7 hours whereby the solution contained a bright yellow precipitate. The reaction was cooled to room temperature and the precipitate collected and dried to produce 2-amino-5 -fluoro-3-nitrobenzoic acid (152 mg, 92%) as a yellow solid.

Method B: A solution containing sodium hydroxide (1.5 g, 38.0 mmol) and water (20 mL) was added to 2-acetamido-5 -fluoro-3-nitrobenzoic acid (2.055 g, 8.50 mmol) and allowed to reflux for 4 hours. The reaction was cooled to 0° C. and the solution was acidified with concentrated hydrochloric acid. The precipitate which developed was collected by filtration and dried to give 2-amino-5 -fluoro-3-nitrobenzoic acid (1.49 g, 88%) as a light yellow solid which is identical in all respects to the compound in Method A.: m.p. 218°–220°; 1H NMR (400 MH$_z$, DMSO-d6) δ 8.04 (dd, 1H), 8.17 (dd, 1H), 8.35 (bs, 1H); 13C NMR (100 MH$_z$, DMSO-d6) δ 118.1, 118.4, 127.5, 127.7, 132.2, 132.3, 144.6, 149.0, 151.4, 168.1; 1R (neat) 3459, 3345, 1687, 1563, 1513, 1440, 1270, 1211 cm-1.

F. 2,3-Diamino-5-Flurobenzoic Acid Dihydrochloride

Method A: A pressure flask capable of withstanding 150 psi. was added 2-amino-5-fluoro-3-nitrobenzoic acid (1.0 g, 5.0 mmol) dissolved in 6M hydrochloric acid (40 mL) and 10% palladium on carbon (100 mg). The reaction was placed in a Parr apparatus and the flask flushed three times with hydrogen leaving an internal pressure of 65 psi. The reaction was continued for 16 hours while maintaining a pressure of 65 psi. The reaction was filtered through celite, washed with cold water and the filtrate evaporated to dryness to give 2,3-diamino-5-fluorobenzoic acid dihydrochloride (962 mg, 79%) as a light brown solid.

Method B: 2,3-diamino-5-fluorobenzoic acid (100 mg, 0.59 mmol) was combined with water (10 mL) in a small reaction vial. To this solution was slowly bubbled hydrogen chloride gas until all the solid dissolved, approximately 30 seconds. The solvents were removed in vacuo to produce a dark solid of 2,3-diamino-5-fluorobenzoic acid dihydrochloride (110 mg, 77%) which was identical in all respects to the sample prepared in Method A.: m.p. 215°– 217° (dec); 1H NMR (400 MH$_z$, D2O) δ 7.11 (dd, 1H), 7.43 (dd, 1H); 13C NMR (100 MH$_z$ D2O) δ 102.4, 102.7, 104.6, 104.8, 109.3, 109.4, 137.0, 138.5, 138.6, 152.0, 154.8, 170.1.

G. 2,3-Diamino-5-Fluorobenzoic Acid

A pressure flask capable of withstanding 150 psi. was added 2-amino-5-fluoro-3-nitrobenzoic acid (1.2 g, 6.0 mmol) dissolved in methanol (40 mL) and 10% palladium on carbon (150 mg). The reaction was placed in a Parr apparatus and the flask flushed three times with hydrogen leaving an internal pressure of 65 psi. The reaction was continued for 17 hours while maintaining a pressure of 65 psi. The reaction was filtered through celite, washed with methanol and the filtrate evaporated to dryness to give 2,3-diamino-5-fluorobenzoic acid (808 mg, 79%) as a dark brown solid.: m.p. 181°–191° (dec); 1H NMR (400 MH$_z$, DMSO-d6 δ 6.43 (dd, 1H), 6.71 (dd, 1H); 13C NMR (100 MH$_z$, DMSO-d6) δ 102.4, 102.7, 104.6, 104.8, 109.3, 109.4, 137.0, 138.5, 138.6, 152.5, 154.8, 170.1.

This invention may be embodied in other forms or carried out in other ways without departing from the spirit or essential characteristics thereof. The present disclosure is therefore to be considered as in all respects illustrative and not restrictive, the scope of the invention being indicated by the appended claims, and all changes which come within the meaning and range of equivalency are intended to be embraced therein.

What is claimed is:

1. A method for inhibiting the advanced glycosylation of a target protein comprising contacting the target protein with an effective amount of composition comprising a compound selected from the group consisting of compounds of the formula

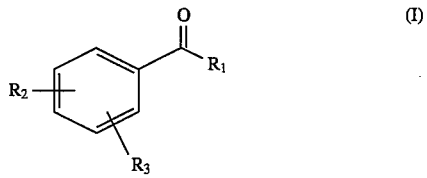

wherein $R_1$ is a hydroxy, lower alkoxy, amino or hydrazino group, or a group of the formula

wherein $R_4$ is hydrogen or lower alkyl, and $R_5$ is an alkyl group of 1–20 carbon atoms, an aryl group, a hydroxy lower alkyl group, a cycloloweralkyl group or a heterocyclic group containing 4–7 ring members and 1–3 heteroatoms; or $R_4$ and $R_5$ together with the nitrogen form a morpholino, piperidinyl, or piperazinyl group; or when $R_4$ is hydrogen, then $R_5$ can also be a hydroxy group;

$R_2$ is 0–3 amino or nitro groups, and/or a hydrazino group, a hydrazinosulfonyl group, a hydroxyethylamino or an amidino group;

$R_3$ is hydrogen or one or two fluoro, hydroxy, lower alkoxy, carboxy, loweralkylamino, dilower alkylamino or hydroxyloweralkylamino groups;

with the proviso that when $R_1$ is hydroxy or lower alkoxy, then $R_3$ is a non-hydrogen substituent;

with the further proviso that when $R_1$ is hydrazino, then there must be at least two non-hydrogen substituents on the phenyl ring;

and with the further proviso that when $R_3$ is hydrogen, then $R_5$ can also be an aminoimino, guanidyl, aminoguanidinyl or diaminoguanidyl group;

their pharmaceutically acceptable salts; and mixtures thereof, and a carrier therefor.

2. The method of claim 1 wherein said compound has the formula wherein $R_2$ is an amino group and $R_3$ is a hydroxy group.

3. The method of claim 2 wherein said compound is 3-amino-4-hydroxybenzhydrazide or a pharmaceutically acceptable salt thereof.

4. The method of claim 2 wherein said compound is 4-amino-3-hydroxybenzoic acid or a pharmaceutically acceptable salt thereof.

5. The method of claim 2 wherein said compound is 3-amino-4-hydroxybenzoic acid or a pharmaceutically acceptable salt thereof.

6. The method of claim 4 wherein said compound is 3-amino-4-hydroxybenzhydrazide hydrochloride or another pharmaceutically acceptable salt thereof.

7. The method of claim 1 wherein said compound has the formula wherein $R_2$ is one or two amino groups.

8. The method of claim 7 wherein said compound is 4-(cyclohexylamino-carbonyl)-o-phenylene diamine monohydrochloride or another pharmaceutically acceptable salt thereof.

9. The method of claim 7 wherein said compound is 4-(butylamino-carbonyl)-o-phenylene-diamine dihydrochloride or another pharmaceutically acceptable salt thereof.

10. The method of claim 7 wherein said compound is 4-(morpholino-carbonyl)-o-phenylene-diamine monohydrochloride or another pharmaceutically acceptable salt thereof.

11. The method of claim 7 wherein said compound is 4-[(4-morpholino)hydrazino-carbonyl]-o-phenylene diamine or a pharmaceutically acceptable salt thereof.

12. The method of claim 7 wherein said compound is 4-(ethylamino-carbonyl)-o-phenylene-diamine dihydrochloride or a pharmaceutically acceptable salt thereof.

13. The method of claim 7 wherein said compound is 4-carbamoyl-o-phenylene diamine hydrochloride or a pharmaceutically acceptable salt thereof.

14. The method of claim 7 wherein said compound is 4-(1-piperidinylamino-carbonyl)-o-phenylenediamine dihydrochloride or a pharmaceutically acceptable salt thereof.

15. The method of claim 7 wherein said compound is 3,4-diaminobenzhydrazide or a pharmaceutically acceptable salt thereof.

16. The method of claim 7 wherein said compound is 4-aminobenzhydrazide or a pharmaceutically acceptable salt thereof.

17. A method for treating an animal to inhibit the formation of advanced glycosylation endproducts of a target protein within said animal, said method comprising administering to an animal in need of said treatment an effective amount of a pharmaceutical composition, said pharmaceutical composition comprising a compound selected from the group consisting of compounds of the formula

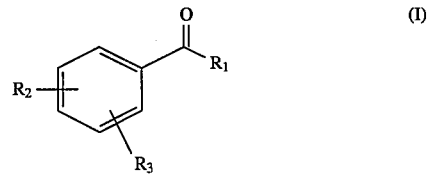

wherein $R_1$ is a hydroxy, lower alkoxy, amino or hydrazino group, or a group of the formula

wherein $R_4$ is hydrogen or lower alkyl, and $R_5$ is an alkyl group of 1–20 carbon atoms, an aryl group, a hydroxy lower alkyl group, a cycloloweralkyl group or a heterocyclic group containing 4–7 ring members and 1–3 heteroatoms; or $R_4$ and $R_5$ together with the nitrogen form a morpholino, piperidinyl, or piperazinyl group; or when $R_4$ is hydrogen, then $R_5$ can also be a hydroxy group;

$R_2$ is 0–3 amino or nitro groups, and/or a hydrazino group, a hydrazinosulfonyl group, a hydroxyethylamino or an amidino group;

$R_3$ is hydrogen or one or two fluoro, hydroxy, lower alkoxy, carboxy, loweralkylamino, diloweralkylamino or hydroxyloweralkylamino groups;

with the proviso that when $R_1$ is hydroxy or lower alkoxy, then $R_3$ is a non-hydrogen substituent;

with the further proviso that when $R_1$ is hydrazino, then there must be at least two non-hydrogen substituents on the phenyl ring;

and with the further proviso that when $R_3$ is hydrogen, then $R_5$ can also be an aminoimino, guanidyl, aminoguanidinyl or diaminoguanidyl group; their pharmaceutically acceptable salts; and mixtures thereof, and a carrier therefor.

18. The method of claim 17 wherein said compound has the formula wherein $R_1$ is an amino group and $R_3$ is a hydroxy group.

19. The method of claim 18 wherein said compound is 3-amino-4-hydroxybenzhydrazide or a pharmaceutically acceptable salt thereof.

20. The method of claim 18 wherein said compound is 4-amino-3-hydroxybenzoic acid or a pharmaceutically acceptable salt thereof.

21. The method of claim 18 wherein said compound is 3-amino-4-hydroxybenzoic acid or a pharmaceutically acceptable salt thereof.

22. The method of claim 19 wherein said compound is 3-amino-4-hydroxybenzyhydrazide hydrochloride.

23. The method of claim 17 wherein said compound has the formula wherein $R_2$ is one or two amino groups.

24. The method of claim 23 wherein said compound is 4-(cyclohexylamino-carbonyl)-o-phenylene diamine monohydrochloride or another pharmaceutically acceptable salt thereof.

25. The method of claim 23 wherein said compound is 4-(butylamino-carbonyl)-o-phenylene-diamine dihydrochloride or a pharmaceutically acceptable salt thereof.

26. The method of claim 23 wherein said compound is 4-(morpholino-carbonyl)-o-phenylene-diamine monohydrochloride or another pharmaceutically acceptable salt thereof.

27. The method of claim 23 wherein said compound is 4-[(4-morpholino)hydrazino-carbonyl]-o-phenylene diamine or another pharmaceutically acceptable salt thereof.

28. The method of claim 23 wherein said compound is 4-(ethylamino-carbonyl)-o-phenylene-diamine dihydrochloride or a pharmaceutically acceptable salt thereof.

29. The method of claim 23 wherein said compound is 4-carbamoyl-o-phenylene diamine hydrochloride or another pharmaceutically acceptable salt thereof.

30. The method of claim 23 wherein said compound is 4-(1-piperidinylamino-carbonyl)-o-phenylenediamine dihydrochloride or a pharmaceutically acceptable salt thereof.

31. The method of claim 23 wherein said compound is 3,4-diaminobenzhydrazide or another pharmaceutically acceptable salt thereof.

32. The method of claim 23 wherein said compound is 4-aminobenzhydrazide or another pharmaceutically acceptable salt thereof.

33. A method of inhibiting the discoloration of teeth resulting from non-enzymatic browning in the oral cavity which comprises administration of an amount effective to inhibit the formation of advanced glycosylation endproducts of a composition comprising a compound selected from the group consisting of compounds of the formula

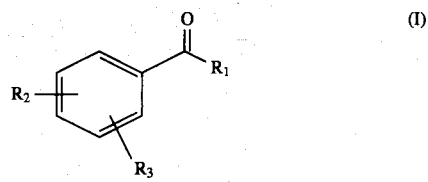
(I)

wherein $R_1$ is a hydroxy, lower alkoxy, amino or hydrazino group, or a group of the formula $-NR_4R_5$, wherein $R_4$ is hydrogen or lower alkyl, and $R_5$ is an alkyl group of 1–20 carbon atoms, an aryl group, a hydroxy lower alkyl group, a cycloloweralkyl group or a heterocyclic group containing 4–7 ring members and 1–3 heteroatoms; or $R_4$ and $R_5$ together with the nitrogen form a morpholino, piperidinyl, or piperazinyl group; or when $R_4$ is hydrogen, then $R_5$ can also be a hydroxy group;

$R_2$ is 0–3 amino or nitro groups, and/or a hydrazino group, a hydrazinosulfonyl group, a hydroxyethylamino or an amidino group;

$R_3$ is hydrogen or one or two fluoro, hydroxy, lower alkoxy, carboxy, loweralkylamino, dilower alkylamino or hydroxyloweralkylamino groups;

with the proviso that when $R_1$ is hydroxy or lower alkoxy, then $R_3$ is a non-hydrogen substituent;

with the further proviso that when $R_1$ is hydrazino, then there must be at least two non-hydrogen substituents on the phenyl ring;

and with the further proviso that when $R_1$ is hydrogen, then $R_5$ can also be an aminoimino, guanidyl, aminoguanidinyl or diaminoguanidyl group;

with the further proviso that when $R_1$ is hydrazino, then there must be at least two non-hydrogen substituents on the phenyl ring;

and with the further proviso that when $R_3$ is hydrogen, then $R_5$ can also be an aminoimino, guanidyl, aminoguanidinyl or diaminoguanidyl group; and their pharmaceutically acceptable salts; and mixtures thereof.

34. A pharmaceutical composition for administration to an animal to inhibit the advanced glycosylation of a target protein within said animal, comprising a pharmaceutically effective amount of a compound selected from the group consisting of compounds of the formula

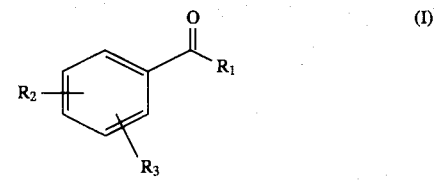
(I)

wherein $R_1$ is a hydroxy, lower alkoxy, amino or hydrazino group, or a group of the formula $-NR_4R_5$, wherein $R_4$ is hydrogen or lower alkyl, and $R_5$ is an alkyl group of 1–20 carbon atoms, an aryl group, a hydroxy lower alkyl group, a cycloloweralkyl group or a heterocyclic group containing 4–7 ring members and 1–3 heteroatoms; or $R_4$ and $R_5$ together with the nitrogen form a morpholino, piperidinyl, or piperazinyl group; or when $R_4$ is hydrogen, then $R_5$ can also be a hydroxy group;

$R_2$ is 0–3 amino or nitro groups, and/or a hydrazino group, a hydrazinosulfonyl group, a hydroxyethylamino or an amidino group;

$R_3$ is hydrogen or one or two fluoro, hydroxy, lower alkoxy, carboxy, loweralkylamino, diloweralkylamino or hydroxyloweralkylamino groups;

with the proviso that when $R_1$ is hydroxy or lower alkoxy, then $R_3$ is a non-hydrogen substituent;

with the further proviso that when $R_1$ is hydrazino, then there must be at least two non-hydrogen substituents on the phenyl ring;

and with the further proviso that when $R_3$ is hydrogen, then $R_5$ can also be an aminoimino, guanidyl, aminoguanidinyl or diaminoguanidyl group; and their pharmaceutically acceptable salts; and mixtures thereof.

35. A compound of the formula

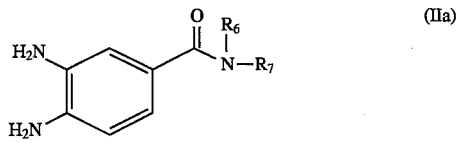

(IIa)

wherein $R_6$ is hydrogen and $R_7$ is a morpholino, piperidinyl, homopiperidinyl, or piperazinyl group; or, $R_6$ and $R_7$, together with the nitrogen atom, form a morpholino, piperidino, or piperazinyl group; and their pharmaceutically acceptable salts.

36. The compound of claim 35 which is 4-(morpholinocarbonyl)-o-phenylene-diamine monohydrochloride or another pharmaceutically acceptable salt thereof.

37. The compound of claim 35 which is 4-[(4-morpholino)hydrazino-carbonyl]-o-phenylenediamine or a pharmaceutically acceptable salt thereof.

38. The compound of claim 35 which is 4-(1-piperidinylamino carbonyl)-o-phenylenediamine dihydrochloride or another pharmaceutically acceptable salt thereof.

39. A compound of the formula

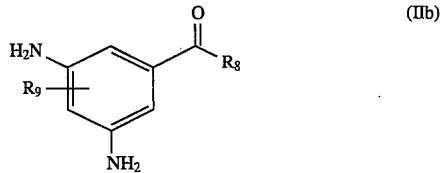

(IIb)

wherein $R_8$ is a hydroxy, alkoxy, hydrazino group, or a group of the formula —$NR_6R_7$ wherein $R_6$ is hydrogen and $R_7$ is a morpholino, piperidinyl, homopiperidinyl, or piperazinyl group;

or, $R_6$ and $R_7$, together with the nitrogen atom, form a morpholino, piperidino, or piperazinyl group; or when $R_6$ is hydrogen, then $R_7$ can also be a phenyl group; $R_9$ is one or two hydroxy, alkoxy, lower alkylamino, diloweralkylamino or hydroxyloweralkylamino groups; with the proviso that when $R_8$ is a hydroxy group, then $R_9$ is a group other than hydroxy; and their pharmaceutically acceptable salts.

40. The compound according to claim 39 which is 3,5-diamino-4-hydroxybenzoic acid or a pharmaceutically acceptable salt thereof.

41. The compound according to claim 39 which is 3,5-diaminosalicylic acid or a pharmaceutically acceptable salt thereof.

42. The compound according to claim 39 which is methyl 3,5-diamino-4-hydroxybenzoate or a pharmaceutically acceptable salt thereof.

43. The compound according to claim 39 which is methyl 3,5-diamino-2,4-dihydroxybenzoate or a pharmaceutically acceptable salt thereof.

44. The compound according to claim 39 which is isopropyl 3,5-diamino-4-hydroxybenzoate or a pharmaceutically acceptable salt thereof.

45. The compound according to claim 39 which is 4-(3,5-diamino-4-hydroxybenzoyl) morpholine or a pharmaceutically acceptable salt thereof.

46. The compound according to claim 39 which is ethyl 3,5-diamino-4-hydroxybenzoate or a pharmaceutically acceptable salt thereof.

47. The compound according to claim 39 which is isopropyl 3,5-diamino-2,4-dihydroxybenzoate or a pharmaceutically acceptable salt thereof.

48. The compound according to claim 39 which is 3,5-diamino-4-hydroxybenzanilide or a pharmaceutically acceptable salt thereof.

49. The compound according to claim 39 which is ethyl 3,5-diamino-4-ethoxybenzoate or a pharmaceutically acceptable salt thereof.

50. The compound according to claim 39 which is isopropyl 3,5-diamino-4-isopropyloxybenzoate or a pharmaceutically acceptable salt thereof.

51. The compound according to claim 39 which is 3,5-diamino-4-methoxybenzoic acid or a pharmaceutically acceptable salt thereof.

52. The compound according to claim 39 which is 3,5-diamino-4-methoxybenzhydrazide or a pharmaceutically acceptable salt thereof.

53. The compound according to claim 39 which is methyl 3,5-diamino-4-methoxybenzoate or a pharmaceutically acceptable salt thereof.

54. The compound according to claim 39 which is 3,5-diamino-4-methylaminobenzoic acid or a pharmaceutically acceptable salt thereof.

55. The compound according to claim 39 which is 3,5-diamino-4-isopropylaminobenzoic acid or a pharmaceutically acceptable salt thereof.

56. The compound according to claim 39 which is 3,5-diamino-4-dimethylaminobenzoic acid or a pharmaceutically acceptable salt thereof.

57. The compound according to claim 39 which is 3,5-diamino-4-isopropyloxybenzhydrazide or a pharmaceutically acceptable salt thereof.

58. The compound according to claim 39 which is 3,5-diamino-4-isopropyloxybenzoic acid or a pharmaceutically acceptable salt thereof.

59. The compound according to claim 39 which is 3,5-diamino-4-hydroxyethylaminobenzoic acid or a pharmaceutically acceptable salt thereof.

60. The compound which is 2,3-diamino-5-fluorobenzoic acid or a pharmaceutically acceptable salt thereof.

* * * * *